United States Patent
Agah et al.

(10) Patent No.: US 10,512,761 B2
(45) Date of Patent: *Dec. 24, 2019

(54) METHODS FOR DELIVERY OF THERAPEUTIC MATERIALS TO TREAT PANCREATIC CANCER

(71) Applicant: RenovoRx, Inc., Los Altos, CA (US)

(72) Inventors: Ramtin Agah, Menlo Park, CA (US);
Imtiaz L. Qureshi, Saratoga, CA (US);
Kamran Najmabadi, Palo Alto, CA (US); Shaun R. Bagai, Mountain View, CA (US)

(73) Assignee: RenovoRx, Inc., Los Altos, CA (US)

( * ) Notice: Subject to any disclaimer, the term of this patent is extended or adjusted under 35 U.S.C. 154(b) by 486 days.

This patent is subject to a terminal disclaimer.

(21) Appl. No.: 15/351,922

(22) Filed: Nov. 15, 2016

(65) Prior Publication Data

US 2017/0056629 A1    Mar. 2, 2017

Related U.S. Application Data

(63) Continuation-in-part of application No. 14/958,415, filed on Dec. 3, 2015, now abandoned, which is a
(Continued)

(51) Int. Cl.
*A61M 25/10* (2013.01)
*A61B 1/273* (2006.01)
(Continued)

(52) U.S. Cl.
CPC ......... *A61M 25/1011* (2013.01); *A61B 1/273* (2013.01); *A61M 25/1002* (2013.01);
(Continued)

(58) Field of Classification Search
CPC .. A61M 25/01; A61M 25/10; A61M 25/1011; A61M 25/1015; A61M 25/007;
(Continued)

(56) References Cited

U.S. PATENT DOCUMENTS 4,445,892 A    5/1984   Hussein et al.
4,655,746 A *  4/1987   Daniels ............... A61M 1/3615
                                                        604/101.04
(Continued)

FOREIGN PATENT DOCUMENTS

EP    0 402 467 A1    12/1990
EP    1 303 228 B1     9/2012
(Continued)

OTHER PUBLICATIONS

US 7,316,661 B2, 01/2008, Zadno-Azizi (withdrawn)
(Continued)

*Primary Examiner* — Andrew M Gilbert

(57) ABSTRACT

Disclosed is a localized method for treatment of cancer including the steps of providing a drug delivery catheter; navigating the catheter to the bile duct; and delivering a therapeutic agent into the bile duct. According to one aspect of the method, the drug delivery catheter is a multi-occlusion balloon catheter. The multi-occlusion balloon catheter may include at least two balloons. The multi-occlusion balloon catheter may optionally include a pressure transducer between the balloons to optimize delivery technique.

14 Claims, 16 Drawing Sheets

Related U.S. Application Data continuation-in-part of application No. 14/870,833, filed on Sep. 30, 2015, now Pat. No. 9,463,304, which is a continuation of application No. 14/293,603, filed on Jun. 2, 2014, now Pat. No. 9,457,171, and a continuation-in-part of application No. 12/958,711, filed on Dec. 2, 2010, now Pat. No. 8,821,476.

(60) Provisional application No. 61/830,218, filed on Jun. 3, 2013, provisional application No. 61/265,845, filed on Dec. 2, 2009.

(51) Int. Cl.
    *A61M 25/00* (2006.01)
    *A61M 25/01* (2006.01)
    *A61M 5/14* (2006.01)
    *A61B 17/12* (2006.01)

(52) U.S. Cl.
    CPC ... *A61B 17/12045* (2013.01); *A61B 17/12136* (2013.01); *A61M 5/14* (2013.01); *A61M 25/007* (2013.01); *A61M 25/0097* (2013.01); *A61M 2025/0004* (2013.01); *A61M 2025/0037* (2013.01); *A61M 2025/0175* (2013.01); *A61M 2025/1015* (2013.01); *A61M 2025/1052* (2013.01); *A61M 2210/00* (2013.01); *A61M 2210/10* (2013.01); *A61M 2210/1042* (2013.01); *A61M 2230/30* (2013.01)

(58) Field of Classification Search
    CPC .. A61M 2025/0004; A61M 2025/0006; A61M 2025/0039; A61M 2025/004; A61M 2025/1015; A61M 2025/1052; A61M 2025/104; A61M 2025/1045; A61M 2210/12; A61M 2210/1122; A61B 6/504; A61B 6/507; A61B 6/481
    See application file for complete search history.

(56) References Cited

U.S. PATENT DOCUMENTS

| | | | |
|---|---|---|---|
| 4,665,746 A * | 5/1987 | Sheppard | G01F 23/167 137/625.46 |
| 4,696,304 A * | 9/1987 | Chin | A61B 5/028 600/486 |
| 4,714,460 A * | 12/1987 | Calderon | A61M 25/00 604/264 |
| 4,830,003 A | 5/1989 | Wolff et al. | |
| 4,883,459 A | 11/1989 | Calderon | |
| 5,281,200 A | 1/1994 | Corso, Jr. et al. | |
| 5,318,535 A | 6/1994 | Miraki | |
| 5,338,301 A | 8/1994 | Diaz | |
| 5,397,307 A | 3/1995 | Goodin | |
| 5,411,479 A | 5/1995 | Bodden | |
| 5,415,636 A | 5/1995 | Forman | |
| 5,419,763 A | 5/1995 | Hildebrand | |
| 5,462,529 A | 10/1995 | Simpson et al. | |
| 5,478,309 A | 12/1995 | Sweezer et al. | |
| 5,484,412 A | 1/1996 | Pierpont | |
| 5,514,092 A | 5/1996 | Forman et al. | |
| 5,575,815 A | 11/1996 | Slepian et al. | |
| 5,772,632 A | 6/1998 | Forman | |
| 5,810,757 A | 9/1998 | Sweezer, Jr. et al. | |
| 5,833,644 A | 11/1998 | Zadno-Azizi et al. | |
| 5,833,650 A | 11/1998 | Imran | |
| 5,833,672 A | 11/1998 | Kawata et al. | |
| 5,836,905 A | 11/1998 | Lemelson et al. | |
| 5,836,967 A | 11/1998 | Schneider | |
| 5,840,066 A * | 11/1998 | Matsuda | A61M 25/104 604/102.02 |
| 5,843,050 A | 12/1998 | Jones et al. | |
| 5,916,193 A | 6/1999 | Stevens et al. | |
| 5,919,163 A | 7/1999 | Glickman | |
| 5,925,016 A | 7/1999 | Chornenky et al. | |
| 5,961,536 A | 10/1999 | Mickley et al. | |
| 5,968,012 A | 10/1999 | Ren et al. | |
| 6,030,362 A | 2/2000 | Boussignac et al. | |
| 6,051,014 A | 4/2000 | Jang | |
| 6,083,198 A | 7/2000 | Afzal | |
| 6,126,635 A | 10/2000 | Simpson et al. | |
| 6,156,053 A | 12/2000 | Gandhi et al. | |
| 6,165,152 A | 12/2000 | Becker et al. | |
| 6,176,844 B1 | 1/2001 | Lee | |
| 6,287,290 B1 | 9/2001 | Perkins et al. | |
| 6,299,598 B1 | 10/2001 | Bander | |
| 6,346,098 B1 | 2/2002 | Yock et al. | |
| 6,351,663 B1 | 2/2002 | Flower | |
| 6,436,090 B1 | 8/2002 | Sanchez et al. | |
| 6,440,097 B1 | 8/2002 | Kupiecki | |
| 6,461,327 B1 | 10/2002 | Addis et al. | |
| 6,482,172 B1 | 11/2002 | Thramann | |
| 6,485,500 B1 | 11/2002 | Kokish et al. | |
| 6,488,672 B1 | 12/2002 | Dance et al. | |
| 6,508,777 B1 | 1/2003 | Macoviak et al. | |
| 6,520,183 B2 | 2/2003 | Amar | |
| 6,569,146 B1 | 5/2003 | Werner et al. | |
| 6,569,148 B2 | 5/2003 | Bagaoisan et al. | |
| 6,575,932 B1 | 6/2003 | O'Brien et al. | |
| 6,589,264 B1 | 7/2003 | Barbut et al. | |
| 6,592,546 B1 | 7/2003 | Barbut et al. | |
| 6,682,499 B2 | 1/2004 | Lenker | |
| 6,685,672 B1 | 2/2004 | Forman | |
| 6,692,458 B2 | 2/2004 | Forman et al. | |
| 6,699,231 B1 * | 3/2004 | Sterman | A61B 17/12045 604/4.01 |
| 6,702,781 B1 | 3/2004 | Reifart et al. | |
| 6,706,013 B1 | 3/2004 | Bhat et al. | |
| 6,706,062 B2 | 3/2004 | Vardi et al. | |
| 6,712,806 B2 | 3/2004 | St Germain et al. | |
| 6,723,070 B1 | 4/2004 | Arai et al. | |
| 6,743,196 B2 | 6/2004 | Barbut et al. | |
| 6,749,581 B2 | 6/2004 | Thompson et al. | |
| 6,884,233 B2 | 4/2005 | Dance et al. | |
| 6,929,633 B2 | 8/2005 | Evans et al. | |
| 6,939,320 B2 | 9/2005 | Lennox | |
| 6,986,788 B2 | 1/2006 | Paul et al. | |
| 6,997,898 B2 | 2/2006 | Forman | |
| 7,150,736 B2 | 12/2006 | Barbut et al. | |
| 7,179,251 B2 | 2/2007 | Palasis | |
| 7,297,475 B2 | 11/2007 | Koiwai et al. | |
| 7,452,532 B2 | 11/2008 | Alt | |
| 7,503,904 B2 | 3/2009 | Choi | |
| 7,537,562 B2 | 5/2009 | Takano | |
| 7,645,259 B2 | 1/2010 | Goldman | |
| 7,708,715 B2 | 5/2010 | Gellman | |
| 7,780,628 B1 | 8/2010 | Keren et al. | |
| 7,815,624 B2 | 10/2010 | Larson | |
| 7,887,661 B2 | 2/2011 | Chiu et al. | |
| 8,043,257 B2 | 10/2011 | Nguyen et al. | |
| 8,088,103 B2 | 1/2012 | Teeslink et al. | |
| 8,162,879 B2 * | 4/2012 | Hattangadi | A61L 29/16 604/101.01 |
| 8,172,792 B2 | 5/2012 | Wang et al. | |
| 8,177,829 B2 | 5/2012 | Benson et al. | |
| 8,182,446 B2 | 5/2012 | Schaeffer et al. | |
| 8,182,463 B2 | 5/2012 | Chiu et al. | |
| 8,187,229 B2 | 5/2012 | Weitzner et al. | |
| 8,251,948 B2 | 8/2012 | Goldman | |
| 8,262,611 B2 | 9/2012 | Teeslink et al. | |
| 8,262,613 B2 | 9/2012 | Lennox | |
| 8,414,473 B2 | 4/2013 | Jenkins et al. | |
| 8,702,678 B2 | 4/2014 | Comerota et al. | |
| 8,784,602 B2 | 7/2014 | Schaeffer et al. | |
| 8,821,476 B2 * | 9/2014 | Agah | A61M 25/007 600/433 |
| 8,870,849 B2 | 10/2014 | Steinmetz et al. | |
| 9,180,281 B2 | 11/2015 | Gerrans et al. | |
| 9,254,210 B2 | 2/2016 | Bourang | |

(56) References Cited

U.S. PATENT DOCUMENTS

| | | | |
|---|---|---|---|
| 9,457,171 B2* | 10/2016 | Agah | A61M 5/142 |
| 9,463,304 B2* | 10/2016 | Agah | A61M 5/142 |
| 10,099,040 B2 | 10/2018 | Agah et al. | |
| 2001/0041862 A1 | 11/2001 | Glickman | |
| 2002/0082548 A1 | 6/2002 | Sanchez et al. | |
| 2002/0107471 A1 | 8/2002 | Thompson et al. | |
| 2002/0115982 A1* | 8/2002 | Barbut | A61B 5/0215 604/509 |
| 2005/0059930 A1 | 3/2005 | Garrison et al. | |
| 2005/0059931 A1* | 3/2005 | Garrison | A61M 25/10 604/101.04 |
| 2005/0149112 A1* | 7/2005 | Barbut | A61B 17/12045 606/200 |
| 2006/0009798 A1 | 1/2006 | Callister et al. | |
| 2006/0149393 A1 | 7/2006 | Calderon | |
| 2006/0200075 A1 | 9/2006 | Zadno-Azizi | |
| 2007/0010782 A1* | 1/2007 | Doty | A61B 17/12045 604/20 |
| 2007/0055132 A1 | 3/2007 | Camus et al. | |
| 2008/0058759 A1 | 3/2008 | Makower et al. | |
| 2008/0269718 A1 | 10/2008 | Wiener et al. | |
| 2009/0018526 A1 | 1/2009 | Power et al. | |
| 2009/0043194 A1 | 2/2009 | Barbut | |
| 2009/0048577 A1 | 2/2009 | Gillies et al. | |
| 2009/0088676 A1 | 4/2009 | Murata | |
| 2009/0131866 A1 | 5/2009 | Zhang et al. | |
| 2009/0264819 A1 | 10/2009 | Diethrich et al. | |
| 2009/0275918 A1 | 11/2009 | Crocker | |
| 2010/0016836 A1 | 1/2010 | Makower et al. | |
| 2010/0106181 A1 | 4/2010 | Gross | |
| 2011/0060276 A1 | 3/2011 | Schaeffer | |
| 2011/0093000 A1 | 4/2011 | Ogle et al. | |
| 2011/0152683 A1 | 6/2011 | Gerrans | |
| 2011/0218494 A1 | 9/2011 | Gerrans | |
| 2011/0257577 A1 | 10/2011 | Lane et al. | |
| 2011/0282195 A1* | 11/2011 | Solar | A61M 25/1002 600/431 |
| 2011/0295114 A1 | 12/2011 | Agah et al. | |
| 2012/0259215 A1* | 10/2012 | Gerrans | A61M 25/1011 600/435 |
| 2014/0214002 A1 | 7/2014 | Lieber et al. | |
| 2014/0276135 A1 | 9/2014 | Agah et al. | |
| 2016/0015948 A1 | 1/2016 | Agah et al. | |
| 2016/0082178 A1 | 3/2016 | Agah et al. | |
| 2017/0157370 A1 | 6/2017 | Agah et al. | |
| 2018/0169067 A1 | 6/2018 | Bascomb et al. | |
| 2018/0333563 A1 | 11/2018 | Agah et al. | |

FOREIGN PATENT DOCUMENTS

| | | |
|---|---|---|
| WO | WO 89/07413 | 8/1989 |
| WO | WO 01/070325 A2 | 9/2001 |
| WO | WO 02/074178 A2 | 9/2002 |
| WO | WO 2011/068946 | 6/2011 |
| WO | WO 2014/197362 A1 | 12/2014 |
| WO | WO 2016/011328 | 1/2016 |
| WO | WO 2018/213760 A1 | 11/2018 |

OTHER PUBLICATIONS

International Search Report and Written Opinion for PCT/US10/58684, dated Feb. 17, 2011.
International Search Report and Written Opinion for PCT/US14/40485, dated Nov. 3, 2014.
European Search Report for European Patent Application No. 10835110.7, dated Mar. 21, 2013.
Office Action for European Patent Application No. 10835110.7, dated Jun. 1, 2015.
Office Action for U.S. Appl. No. 12/958,711, dated Aug. 20, 2013.
Office Action for U.S. Appl. No. 12/958,711, dated Mar. 7, 2014.
Office Action for U.S. Appl. No. 14/293,603, dated Dec. 15, 2015.
Office Action for U.S. Appl. No. 14/870,833, dated Dec. 14, 2015.
Office Action for U.S. Appl. No. 14/293,603, dated May 10, 2016.
Office Action for U.S. Appl. No. 14/870,833, dated May 9, 2016.
Office Action for U.S. Appl. No. 14/958,428, dated Apr. 6, 2016.
Office Action for U.S. Appl. No. 14/958,415, dated Mar. 2, 2016.
Office Action for U.S. Appl. No. 14/958,415, dated Jun. 22, 2016.
Final Office Action issued by The United States Patent and Trademark Office for U.S. Appl. No. 14/958,428, dated Sep. 1, 2016, 20 pages.
Office Action issued by The United States Patent and Trademark Office for U.S. Appl. No. 14/958,428, dated Apr. 20, 2017, 14 pages.
Final Office Action issued by The United States Patent and Trademark Office for U.S. Appl. No. 14/958,428, dated Jan. 22, 2018, 35 pages.
Examination Report issued by the European Patent Office for Application No. 10835110.7, dated Apr. 25, 2018, 4 pages.
Office Action issued by the Indian Patent Office for Application No. 1632/MUMNP/2012, dated Jul. 26, 2018, 6 pages including English translation.
International Search Report and Written Opinion issued by the International Searching Authority for Application No. PCT/US2018/033482, dated Aug. 24, 2018 14 pages.
Anonymous: Researchers Report Survival Benefits with Use of RenovoCathTM in Patients with Locally Advanced Pancreatic Tumors, Renovo Rx (Apr. 19, 2017), Retrieved from the Internet: URL:http://renovorx.com/researchers-report-survival-benefits-use-renovocath-patients-locally-advanced-pancreatic-tumors/ [retrieved on Jul. 24, 2018], 2 pages.
Mahadevan et al., "Stereotactic Body Radiotherapy and Gemcitabine for Locally Advanced Pancreatic Cancer," Int. J. Radiation Oncology Biol. Phys. 78(3):735-742 (2010).
RenovoRx: "RenovoCath Animation", Dec. 17, 2014 (Dec. 17, 2014), Retrieved from the Internet: URL:https://www.youtube.com/watch?v=LFZ7tv Cu2a4&feature=youtu.be [retrieved on Aug. 7, 2018], 1 page.
Anonymous: "RenovoCath for Targeted Fluid Delivery Into Peripheral Vasculature Cleared in Europe", Medgadget Oct. 23, 2015 (Oct. 23, 2015), Retrieved from the Internet: URL:https://www.medgadget.com/2015/10/renovocath-targeted-fluid-delivery-peripheral-vasculature-cleared-europe.html [retrieved on Jul. 25, 2018], 2 pages.
Office Action for European Patent Application No. 10835110.7, dated Jan. 25, 2017.

* cited by examiner

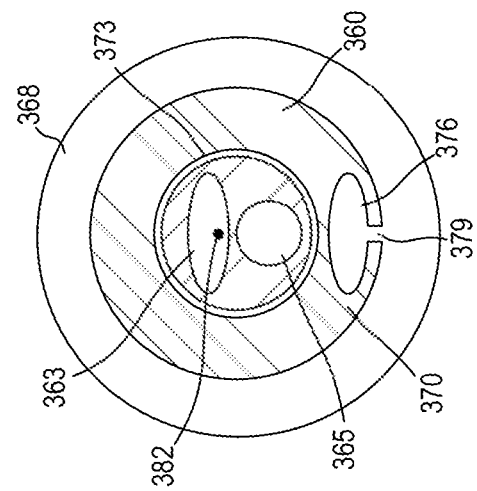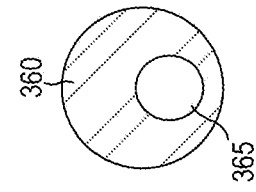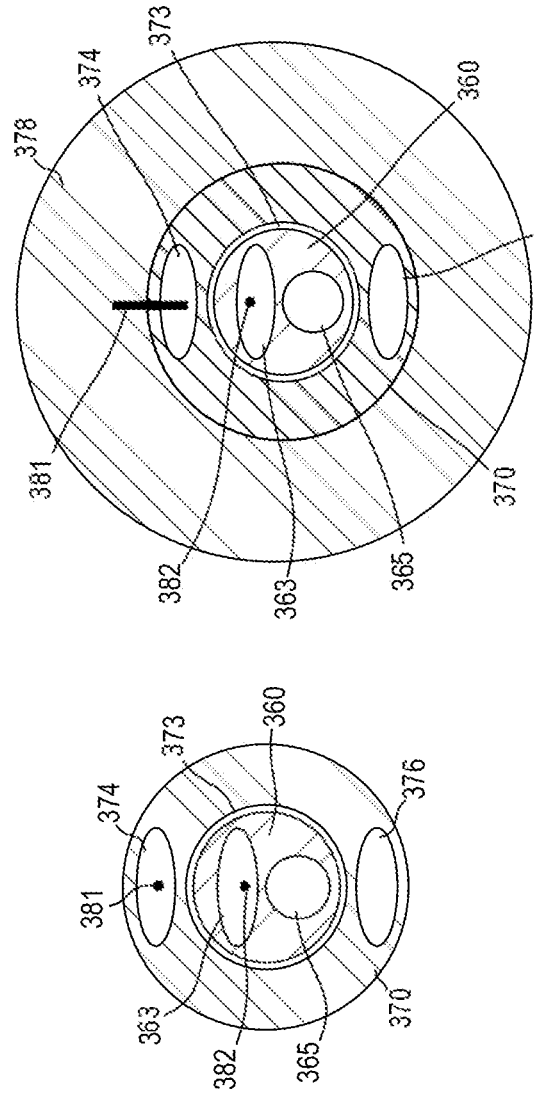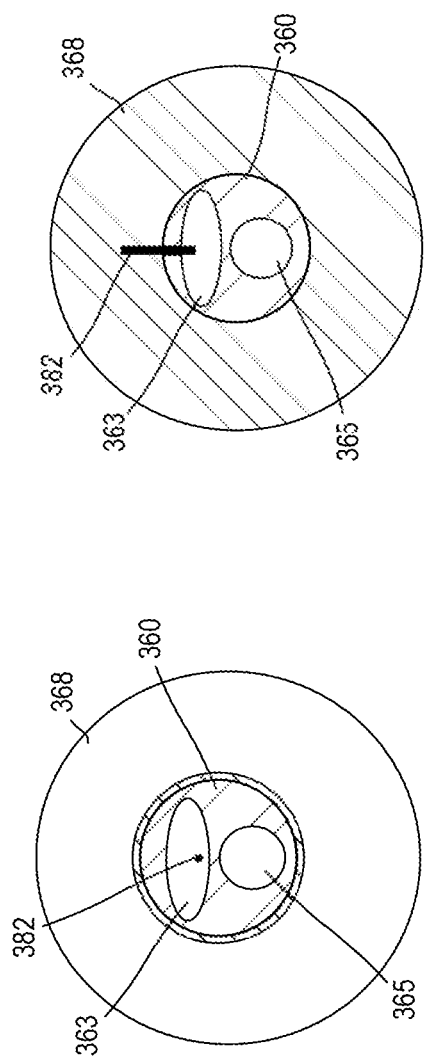

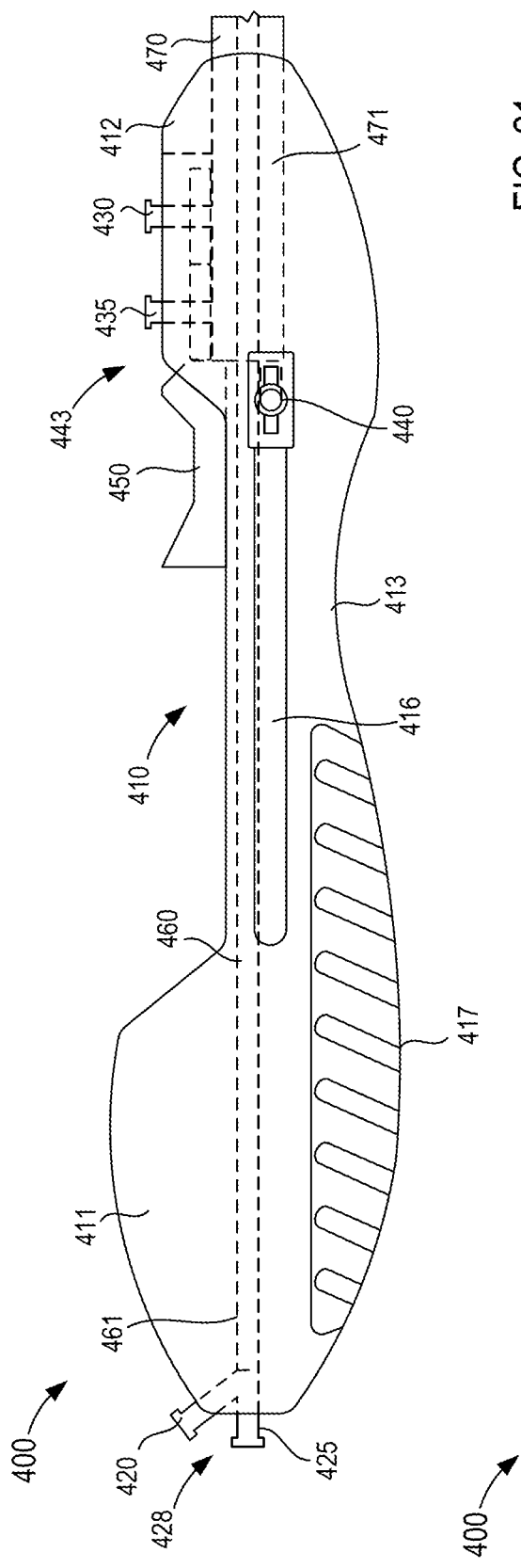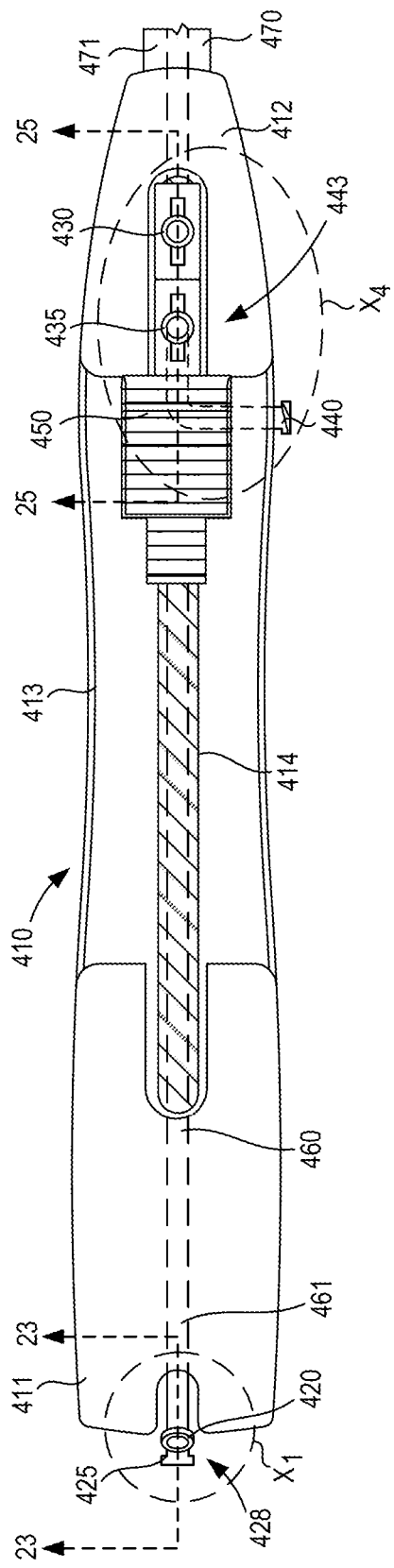

METHODS FOR DELIVERY OF THERAPEUTIC MATERIALS TO TREAT PANCREATIC CANCER

CROSS-REFERENCE TO RELATED APPLICATIONS

This application is a continuation in part of Ser. No. 14/958,415 filed on Dec. 3, 2015, which claims priority to and the benefit of Ser. No. 14/870,833 filed on Sep. 30, 2015 (now U.S. Pat. No. 9,463,304) which is claims priority to and the benefit of U.S. patent application Ser. No. 14/293, 603, entitled "Devices, Methods and Kits for the Delivery of Therapeutic Materials to a Pancreas," filed Jun. 2, 2014 (now U.S. Pat. No. 9,457,171), which claims priority to and the benefit U.S. Provisional Patent Application No. 61/830, 218, entitled "Apparatus and Methods for Insertion and Manipulation of Multi-Occlusion Catheter Device," filed Jun. 3, 2013, and which is also a continuation-in-part of U.S. patent application Ser. No. 12/958,711, entitled "Devices, Methods and Kits for the Delivery of Therapeutic Materials to a Pancreas," filed Dec. 2, 2010 (now U.S. Pat. No. 8,821,476), which claims priority to and the benefit of U.S. Provisional Patent Application No. 61/265,845 entitled "A Catheter System Adapted for Endovascular Delivery of Therapeutic Materials to a Mammalian Pancreas, Method of Treatment of Diabetes, and Kits Therefore," filed Dec. 2, 2009, each of the disclosures of which is incorporated herein by reference in its entirety.

BACKGROUND

The embodiments described herein relate generally to methods for delivering a therapeutic material to treat pancreatic cancer.

Pancreatic cancer is considered an almost chemoresistant tumor. The ineffective result of systemic chemotherapy is at least in part due to an insufficient drug concentration within the tumor because of dose-limited toxicity in bone marrow and epithelial tissue. Since systemic chemotherapy is limited its effectiveness, localized therapy can be desirable for advanced pancreatic cancer patients. For example, one such treatment can include local intra-arterial delivery of chemotherapy. Intra-arterial infusion allows higher drug concentration to reach the tumor, overcoming the problem of poor blood flow to tumor mass in comparison to healthy tissue. Furthermore, intra-arterial chemotherapy can also take advantage of the first pass effect of chemotherapeutics, generating higher-level drug concentrations at the tumor cell membrane and therefore, enhancing cellular drug uptake as compared to intravenous infusion. Lastly, local delivery can reduce systemic side effects.

Such a chemotherapy treatment is usually administered through catheters placed in the celiac/hepatic artery or portal vein, however, a best mode of catheter placement has yet to be established. The tumor response rates of pancreatic arterial infusion chemotherapy can range widely, for example, from 7% to 65%, at least in part due to efficacy of drug delivery where anticancer drugs were administered via the celiac artery without assessment of drug distribution. Thus, a need exists for improved methods for delivering a treatment such as a biologic agent and/or drug formation to target tissue of the pancreas, as well as hepatic tumors and cholangiocarinoma.

SUMMARY

Disclosed is a localized method for treatment of cancer, comprising the steps of: providing a drug delivery catheter; navigating the catheter to the bile duct; delivering a therapeutic agent into the bile duct.

According to one aspect of the aforementioned method, wherein the drug delivery catheter is a multi-occlusion balloon catheter. The multi-occlusion balloon catheter may comprise at least two balloons. The multi-occlusion balloon catheter may optionally include a pressure transducer between the balloons to optimize delivery technique.

According to one aspect of the aforementioned method, the therapeutic agent is selected from the group (5-fluorouracil (5-FU), Aldesleukin, Axitinib, Bleomycin, Carboplatin, Cetuximab, Cisplatin, Cyclophosphamide, Dacarbazine, Doxorubicin Hydrochloride, doxorubicin liposomal non-pegylated (un-coated), doxorubicin liposomal pegylated (PEG coated), Floxuridine, Gemcitabine Hydrochloride, Irinotecan Hydrochloride Liposome, Lanreotide Acetate, leucovorin (antidote to folic acid antagonist used with 5FU), Methotrexate, Mitomycin, Mitoxantrone, Nivolumab, Olaparib, Oxaliplatin, Sorafenib Tosylate, Temsirolimus, Thiotepa, Topotecan Hydrochloride, Vinblastine Sulfate, vincristine sulfate).

According to one aspect of the aforementioned method, the navigating step includes navigating the catheter using ERCP.

According to one aspect of the aforementioned method, the navigating step includes navigating the catheter to the bile duct percutaneously.

According to one aspect of the aforementioned method, the localized method is used to treat pancreatic cancer.

According to one aspect of the aforementioned method, the localized method is used to treat at least one of hepatic tumors and cholangiocarinoma.

BRIEF DESCRIPTION OF THE DRAWINGS

FIGS. 14-19 are each a cross-sectional view of a different portion of the multi-occlusion catheter insertion device taken along lines 14-14, 15-15, 16-16, 17-17, 18-18, and 19-19, respectively, in FIG. 13.

FIG. 21 is a side view of a handle included in the multi-occlusion catheter insertion device of FIG. 20.

FIG. 22 is a top view of a handle included in the multi-occlusion catheter insertion device of FIG. 20.

DETAILED DESCRIPTION

Figure 1:
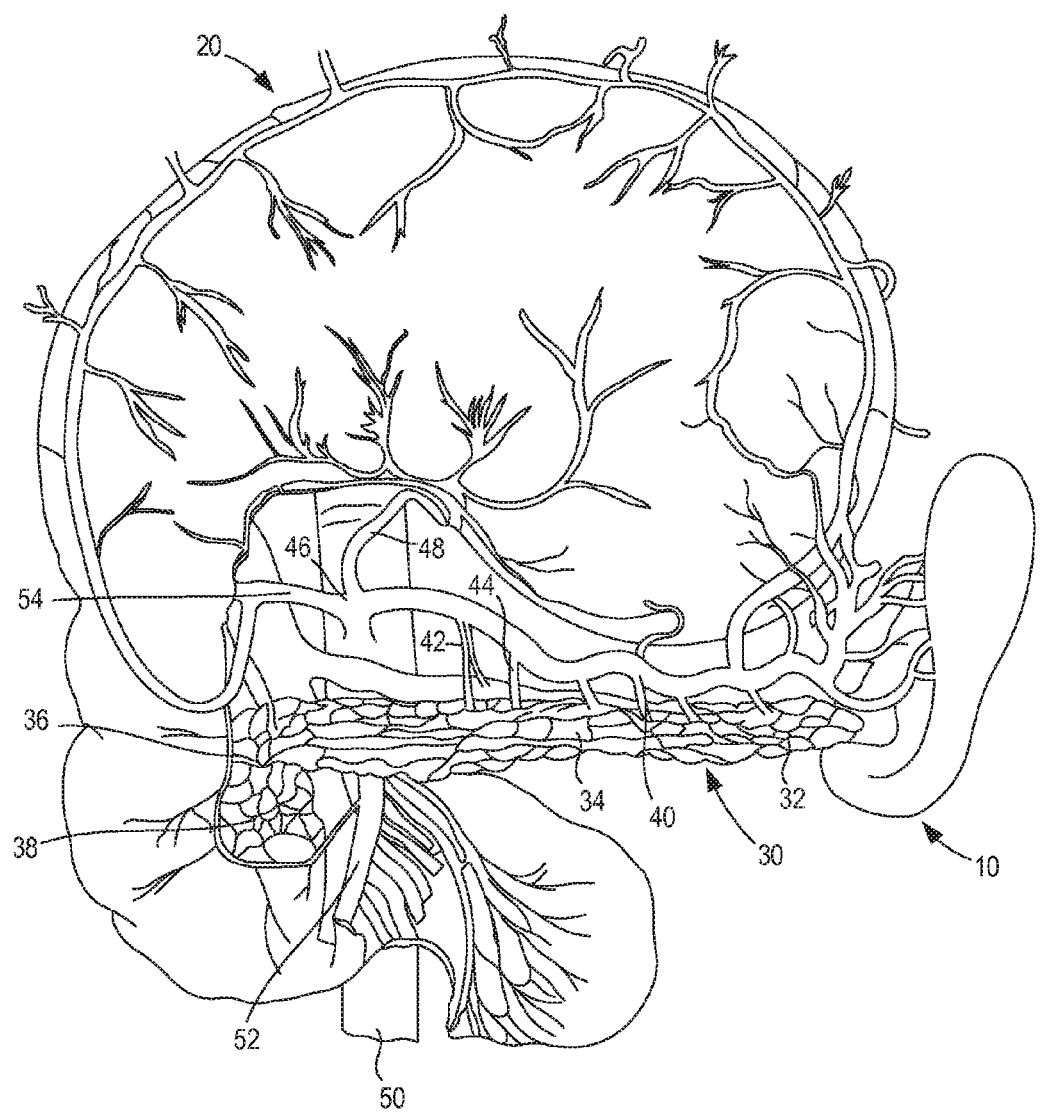
FIG. 1 is an illustration of a pancreas and related structure in a human.

Methods described herein can be used, for example, for the insertion and manipulation of a multi-occlusion catheter device to deliver a therapeutic agents to the bile duct for treatment of pancreatic cancer or other localized cancer. Tumors localized around the bile duct (cancer of the pancreatic head, primary and secondary liver tumors, and cholangiocarcinoma) may benefit from localized delivery through the bile duct itself. The bile duct can be exogenously accessed through an endoscopic retrograde cholangiopancreatogram (ERCP) catheter, one can envision delivery of a double balloon catheter into the bile duct using established ERCP technique. After localizing the double balloon catheter to the area of bile duct involved/adjacent to the tumor, that area of bile duct is isolated by inflating the two balloon elements. Chemotherapeutic elements are then infused between the two balloons. By increasing the pressure between two balloon elements to exceed the interstitial tissue pressure, in a diffusion dependent manner, the chemotherapeutic agent will then diffuse out the wall of the bile duct and into the tissue.

By monitoring and/or adjusting the pressure between the balloons, one can change the penetration depth of the chemotherapy into the tissue.

According to some embodiments, a therapeutic material for treatment of pancreatic cancer or other localized cancer is delivered into the bile duct using the multi-occlusion catheter. The gall bladder is connected to the pancreas via the common bile duct. Localized delivery to the site of the tumor has advantages for both maximizing local drug concentration at the tumor site, and decreasing systemic side effects/toxicity. Thus the approach disclosed herein may avoid some of the toxicity related side effects of delivering chemotherapy drugs directly to the pancreas and may enable the use of more concentrated dosage of chemotherapy drugs. It should be understood that therapeutic particles may be substituted for or used in conjunction with chemotherapy drugs. Moreover, it should be understood that in some cases it may be useful to place a stent to open the bile duct prior to delivering the chemotherapy and/or therapeutic agent.

By way of example, such a use can include navigating a catheter such as a multi-occlusion catheter to the target anatomy using conventional percutaneous approaches or the same approach used for endoscopic retrograde cholangiopancreatogram (ERCP), isolating the bile duct, and then exogenously introducing therapeutic cells/agents/biologics into the isolated area, via an infusion port of the catheter. In such fashion, the cells/agents biologics can be delivered to the bile duct with high efficiency. In some embodiment, a device with two sliding balloon catheters can be used to isolate bile duct. The isolated area can then be perfused with cells/therapeutic agents via an infusion port disposed between the two balloon catheters. In some embodiments, the devices described herein can be arranged such that a user can manipulate a portion of the device substantially single handedly, to allow for accurate delivery of a biological agent and/or drug formulation to an isolated segment or portion of an organ.

This application incorporates by reference to co-pending U.S. application Ser. No. 14/958,415 filed on Dec. 3, 2015.

In some embodiments, an apparatus includes a handle, an inner catheter, an outer catheter, an actuator, a first occlusion element, and a second occlusion element. The inner catheter is coupled to the handle and the first occlusion element is coupled to the inner catheter. The inner catheter defines an inner catheter lumen that is configured to receive a guidewire. The outer catheter is coupled to the housing and the second occlusion element is coupled to the outer catheter. The outer catheter defines a first lumen that is in fluid communication with a distal opening and is configured to introduce a therapeutic agent through the distal opening into the bile duct. The outer catheter defines a second lumen that is configured to receive at least a portion of the inner catheter.

The actuator is coupled to the handle and is configured to move the outer catheter relative to the handle. The second occlusion element is disposed proximal to the first occlusion element and a distance therebetween is adjustable when the outer catheter is moved relative to the handle by the actuator.

In some embodiments, an apparatus includes a handle, an inner catheter, an outer catheter, a first occlusion element, a second occlusion element, and an actuator. The inner catheter is coupled to the handle and the first occlusion element is coupled to the inner catheter. The outer catheter is coupled to the housing and the second occlusion member is coupled to the outer catheter. The outer catheter defines a first lumen that is in fluid communication with a distal opening and that is configured to introduce a therapeutic agent therethrough and into the bile duct. The outer catheter defines a second lumen that is configured to receive at least a portion of the inner catheter. The second occlusion element is disposed proximal of the first occlusion element. The actuator is coupled to the handle and is configured to move the outer catheter relative to the handle between a first position in which the second occlusion element is at a first distance from the first occlusion element and a second position in which the second occlusion element is at a second distance from the first occlusion element, with the second distance being greater than the first distance.

In some embodiments, a system and/or device(s) is provided for endovascular introduction of therapeutic materials selectively to the bile duct for the treatment of pancreatic cancer. In some embodiments, a device and/or system can include, for example, an inner catheter having a distal retractable occlusion element and an inner catheter lumen adapted and configured to introduce a guidewire, and an outer catheter having a distal retractable occlusion element, an infusion lumen adapted and configured to introduce therapeutic materials to the bile duct, and a lumen for slidably receiving the inner catheter. In such an embodiment, the distal retractable occlusion element of the outer catheter can be positioned proximal to the distal retractable occlusion element of the inner catheter; and a sealing element can be included that is configured to selectively isolate or seal an end of the outer catheter to prevent therapeutic materials from entering into the lumen of the outer catheter in which the inner catheter is slidably disposed.

In some embodiments, a selective sealing element can include, for example, a ring, a membrane, or any other suitable element configured to prevent loss of therapeutic material into the lumen of the outer catheter in which the inner catheter is disposed. The lumen provided in the inner catheter can be configured to perfuse a distal organ beyond the targeted isolation region of the artery.

In some embodiments, a distance between the proximal retractable occlusion element and the selective sealing element can be configured for external adjustment, thus allowing a user to customize the isolated area (between the two occlusion elements) to better target the bile duct during delivery of biologics. The proximal retractable occlusion element and the selective sealing element can have a cross-sectional diameter, for example, between 2-12 mm.

In some embodiments, the devices and methods described herein can be used for isolating the perfusion area of the gall bladder for introduction of chemotherapy for treatment of pancreatic cancer, hepatic tumors and cholangiocarinoma or other therapeutic agents targeted to the pancreas.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the term "set" can refer to multiple features or a singular feature with multiple parts. For example, when referring to a set of ports, the set of ports can refer to a single port or to multiple ports.

As used herein, the words "proximal" and "distal" refer to a direction closer to and away from, respectively, an operator of, for example, a medical device. Thus, for example, the end of the medical device closest to the patient's body (e.g., contacting the patient's body or disposed within the patient's body) would be the distal end of the medical device, while the end opposite the distal end and closest to, for example, the user of the medical device, would be the proximal end of the medical device. Said another way, the distal end portion is the end that is located furthest from a point of reference, such as an origin or a point of attachment. For example, the distal end portion would be the end farthest away from a user's hand. The proximal end portion, thus, would be the position nearer to a point of reference such as an origin, i.e., the user's hand.

Table 1 is a list of chemotherapy drugs which may be delivered to the bile duct according to the method of the present invention.

TABLE 1

| # | Drug | Trade Name(s) | Common Indication(s) | Solvents/Diluents |
|---|---|---|---|---|
| 1 | 5-fluorouracil (5-FU) | 5FU, Flourouracil, Adrucil | Breast, Liver, Pancreatic, Stomach | water |
| 2 | Aldesleukin | Proleukin | Kidney | water |
| 3 | Axitinib | Inlyta | Kidney | water |
| 4 | Bleomycin | Blenoxane | Cervical, Testicular | water |
| 5 | Carboplatin | Paraplatin | Ovarian | water |
| 6 | Cetuximab | Erbitux | Colorectal, Head, Neck | water |
| 7 | Cisplatin | Platinol-AQ | Bladder, Liver, Ovarian, Pancreatic, Testicular | water |
| 8 | Cyclophosphamide | Cytoxan | Breast, Ovarian, Pancreatic | water |
| 9 | Dacarbazine | DTIC-Dome | Pancreatic | water |
| 10 | Doxorubicin Hydrochloride | Adriamycin, Rubex, Caelyx | Breast, Liver, Ovarian, Pancreatic, Stomach | water (pH = 3) |
| 11 | doxorubicin liposomal, non-pegylated (uncoated) | Myocet | Breast, Liver, Ovarian, Pancreatic, Stomach | water (pH = 3) |
| 12 | doxorubicin liposomal, pegylated (PEG coated) | Doxil | Breast, Liver, Ovarian, Pancreatic, Stomach | water (pH = 3) |
| 13 | Floxuridine | FUDR | Liver, Pancreatic | water |
| 14 | Gemcitabine Hydrochloride | Hospira, Gemcitab, Gemzar | Breast, Ovarian, Pancreatic | water (pH = 3) |
| 15 | Irinotecan Hydrochloride Liposome | Onivyde, Camptosar | Pancreatic | water (pH = 3) |
| 16 | Lanreotide Acetate | Somatuline Depot | Pancreatic | water |
| 17 | leucovorin (antidote to folic acid antagonist used with 5FU) | | Pancreatic | water or oral |
| 18 | Methotrexate | Otrexup, Rheumatrex, Trexall | Breast, Pancreatic | water |
| 19 | Mitomycin | Mutamycin, MMC, Mitomycin C, Mitozytrex | Liver, Pancreatic, Stomach | water |
| 20 | Mitoxantrone | Novantrone | Pancreatic | water |
| 21 | Nivolumab | Opdivo | Kidney | water |

TABLE 1-continued

| # | Drug | Trade Name(s) | Common Indication(s) | Solvents/Diluents |
|---|---|---|---|---|
| 22 | Olaparib | Lynparza | Ovarian | water |
| 23 | Oxaliplatin | Elotaxin | Pancreatic | water |
| 24 | Sorafenib Tosylate | Nexavar | Kidney | water |
| 25 | Temsirolimus | Torisel | Kidney | water |
| 26 | Thiotepa | | Bladder, Ovarian | water |
| 27 | Topotecan Hydrochloride | Hycamtin | Cervical, Ovarian | water (pH = 3) or oral |
| 28 | Vinblastine Sulfate | Velban, Velsar | Breast, Pancreatic, Testicular | water |
| 29 | vincristine sulfate | Alcrist, Biocristin, Oncocristin-AQ, VCR | Pancreatic | water |

FIG. 1 illustrates the liver 10, the gall bladder 20, and the pancreas 30 situated within an abdominal cavity (not shown) of a mammal (e.g., a human). The pancreas 30 is a gland organ which is part of the digestive and endocrine system of vertebrates. The pancreas 30 is both an endocrine gland producing hormones, including insulin, glucagon, and somatostatin, as well as an exocrine gland, secreting pancreatic juice containing digestive enzymes that pass to the small intestine. These enzymes help in the further breakdown of the carbohydrates, protein, and fat in the chyme.

As shown, the common bile duct leads from the gall bladder to the pancreas 30.

Figure 2:
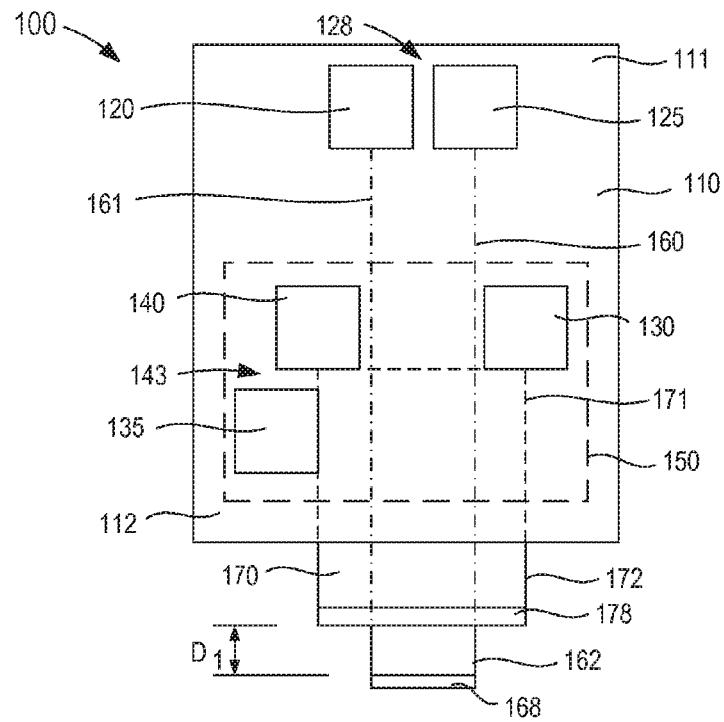
FIGS. 2 and 3 are schematic illustrations of a multi-occlusion catheter insertion device according to an embodiment, in a first configuration and a second configuration, respectively.
Figure 3:
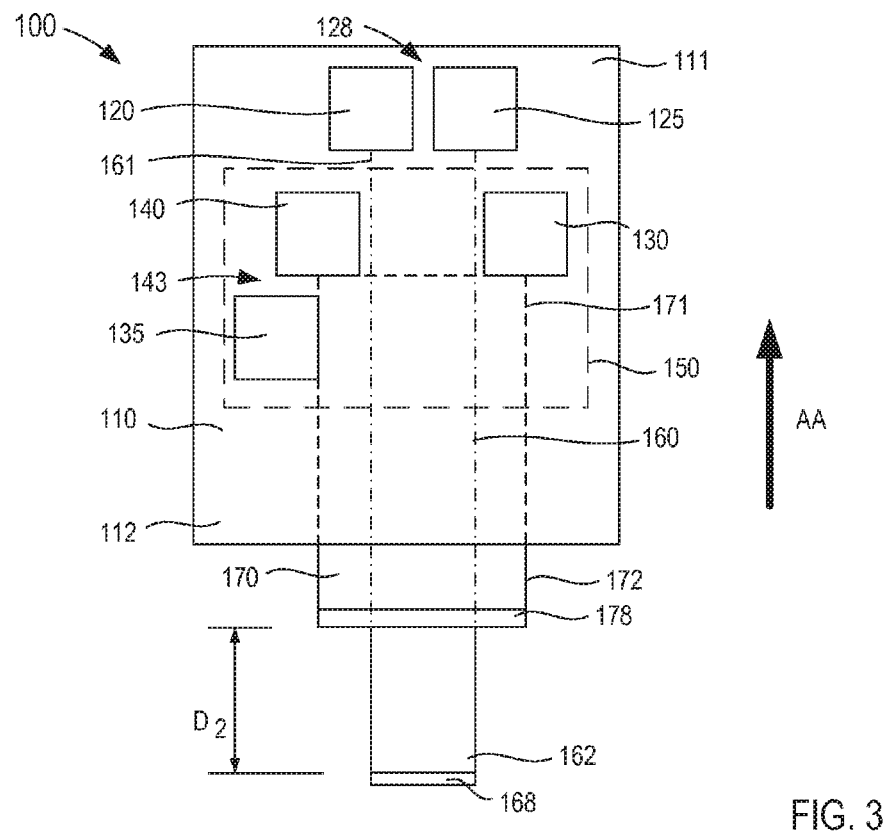

FIGS. 2 and 3 are schematic illustrations of a multi-occlusion catheter insertion device 100 useful for delivering therapeutic agents to the bile duct for treatment of pancreatic cancer. The multi-occlusion catheter insertion device 100 (also referred to herein as "device") can be arranged to allow for substantially single handed use to, for example, isolate a segment of a bodily lumen such as the buke duct, thereby allowing a procedure to be performed within the isolated segment and/or allowing a targeted delivery of a biological or therapeutic agent. The device 100 includes a handle 110, an actuator 150, a first catheter 160, and a second catheter 170. The handle 110 can be any suitable shape, size, or configuration. For example, in some embodiments, the handle 110 can have a shape and size that are configured to enhance the ergonomics of the device 100. As described in further detail herein, the handle 110 can be grasped by a user to insert a portion of the first catheter 160 and a portion of the second catheter 170 into a bodily lumen of a patient and can be manipulated to move, inflate, deflate, adjust, and/or otherwise reconfigure the portion of the first catheter 160 and the portion of the second catheter 170 within the bodily lumen. For example, the second catheter 170 can be moved relative to the first catheter 160, or vice-versa, to adjust a distance between a first occlusion element 168 coupled to a distal end portion of the first catheter 160 and a second occlusion element 178 coupled to a distal end portion of the second catheter 170. The device 100 can be used to isolate a segment of the bile duct within the space defined between the first occlusion element 168 and the second occlusion element 178. Thus, a procedure can then be performed within the isolated segment such as for example, delivering a therapeutic agent to the isolated segment.

The handle 110 has a proximal end portion 111 and a distal end portion 112. As described in further detail herein, the handle 110 can be arranged to enclose, house, and/or be disposed about a portion of the first catheter 160 and the second catheter 170. For example, the first catheter 160 and the second catheter 170 can each be coupled to the handle 110. A first port 120 and a second port 125 (collectively referred to herein as a first set of ports 128) are each disposed at the proximal end portion 111 of the handle 110. The first port 120 and the second port 125 can each define a lumen (not shown in FIGS. 2 and 3). In some embodiments, the first port 120 and the second port 125 can be formed monolithically or integrally with the first catheter 160. The first port 120 and the second port 125 can be any suitable size, shape, or configuration. For example, in some embodiments, the first port 120 and the second port 125 can extend from the proximal end portion 111 of the housing 110 such that at least a portion of the first port 120 and the second port 125 is accessible outside of the handle 110. Although not shown in FIGS. 2 and 3, the first port 120 and the second port 125 can each be physically and fluidically coupled to a device, mechanism, and/or the like, such as, for example, a source of an inflation medium as described in more detail below. For example, in some embodiments, the first port 120 and the second port 125 can each include a Luer-Lok® or the like that can physically and fluidically couple the first port 120 and/or the second port 125 to such a device. As described in further detail herein, the first set of ports 128 can be in fluid communication with at least a portion of the first catheter 160 to place at least the portion of the first catheter 160 in fluid communication with a device (e.g., a source of an inflation medium) coupled to the handle 110 via the first port 120 and/or the second port 125. For example, the lumen of the first port 120 can be in fluid communication with a first lumen defined by the first catheter 160 and the lumen of the second port 125 can be in fluid communication with a second lumen defined by the first catheter 160.

The distal end portion 112 of the handle 110 includes a third port 130, a fourth port 135, and a fifth port 140 (collectively referred to herein as a second set of ports 143). The second set of ports 143 can be any suitable arrangement such as, for example, described above with reference to the first set of ports 128. For example, the third port 130, the fourth port 135, and the fifth port 140 can each define a lumen (not shown in FIGS. 2 and 3) and can each include a Luer-Lok® or the like that can physically and fluidically couple the third port 130, the fourth port 135, and/or the fifth port 140 to any suitable attachment, device, mechanism, and/or the like. For example, the third port 130, the fourth port 135, and/or the fifth port 140 can each be coupled to an external device such as a device supplying a therapeutic agent, a device supplying an inflation medium or a device supplying an irrigation solution as described in more detail below with reference to, for example, device 400. In some embodiments, the second set of ports 143 includes the fifth port 140 and only one of the third port 130 and the second port 135.

As described in further detail herein, the second set of ports 143 can be in fluid communication with at least a portion of the second catheter 170 to place at least the portion of the second catheter 170 in fluid communication with such external devices coupled to the handle 110 via the third port 130, the fourth port 135, and/or the fifth port 140. For example, the third port 130 and/or the fourth port 135 can be coupled to and in fluid communication with a first lumen defined by the second catheter 170, and the fifth port 140 can be coupled to and in fluid communication with a second lumen defined by the second catheter 170. In some embodiments, the third port 130, the fourth port 135, and/or the fifth port 140 can be monolithically or integrally formed with the second catheter 170. Moreover, the second set of ports 143 can be coupled to or operably coupled to the actuator 150 as described in more detail herein.

The first catheter 160 (also referred to herein as "inner catheter") and the second catheter 170 (also referred to herein as "outer catheter") can be any suitable catheter device. For example, in some embodiments, the first catheter 160 and the second catheter 170 are multi-lumen catheters. As shown in FIG. 2, the first catheter 160 has a proximal end portion 161 and a distal end portion 162. The proximal end portion 161 of the first catheter 160 is disposed within a portion of the handle 110. More specifically, the proximal end portion 161 of the first catheter 160 can be fixedly disposed within the portion of the handle 110 to place the first catheter 160 in fluid communication with one or more of the ports 120 and 125 of the first set of ports 128. In some embodiments, the first catheter 160 can define a first lumen that can be physically and fluidically coupled to the first port 120 and a second lumen that can be physically and fluidically coupled to the second port 125. In other embodiments, a first catheter can be coupled to the handle and can be operably coupled to a first port and a second port (e.g., ports 120, 125) via an intervening structure such as, for example, flexible tubing or the like. In this manner, the first port 120 can be placed in fluid communication with a first lumen (not shown in FIGS. 2 and 3) defined by the first catheter 160, as described in further detail herein. Similarly, the second port 125 can be placed in fluid communication with a second lumen (not shown in FIGS. 2 and 3) defined by the first catheter 160. In some embodiments, the second port 125 and the second lumen of the first catheter 160 can receive a guidewire or the like, as described in further detail herein.

The distal end portion 162 of the first catheter 160 extends beyond a distal end portion of the handle 110 and includes the occlusion member 168. The occlusion member 168 can be any suitable device or mechanism that is configured to selectively limit, block, obstruct, or otherwise occlude a bodily lumen in which the occlusion member 168 is disposed. For example, in some embodiments, the occlusion member 168 can be an inflatable balloon or the like that can be transitioned between a collapsed (e.g., deflated) configuration and an expanded (e.g., inflated) configuration. In some embodiments, the arrangement of the first catheter 160 and the handle 110 can be such that the first port 120 is in fluid communication with the occlusion member 168. Thus, in use, the first port 120 can be fluidically coupled to a device that can supply a pressurized fluid (e.g., air, inert gas, or liquid) to the occlusion member 168 to transition the occlusion member 168 between a collapsed configuration and an expanded configuration, as described in further detail herein.

The second catheter 170 of the device 100 has a proximal end portion 171 and a distal end portion 172. As shown in FIGS. 2 and 3, the second catheter 170 is movably disposed about a portion of the first catheter 160. More specifically, the second catheter 170 can be, for example, a multi-lumen catheter and can be arranged such that the first catheter 160 is movably disposed within a first lumen (not shown in FIGS. 2 and 3) defined by the second catheter 170. The proximal end portion 171 can be movably disposed within the handle 110 such that a portion of the second catheter 170 is in fluid communication with the second set of ports 143. In some embodiments, the second catheter 170 can be physically and fluidically coupled to the third port 130 and the fourth port 135, and/or the fifth port 140. In other embodiments, the second catheter can be disposed within a handle and can be operably coupled to one or more ports via an intervening structure such as, for example, flexible tubing or the like. In this manner, the third port 130 and/or the fourth port 135 can be placed in fluid communication with the second lumen (not shown in FIGS. 2 and 3) defined by the second catheter 170, as described in further detail herein; the fifth port 140 can be placed in fluid communication with a third lumen (not shown in FIGS. 2 and 3) defined by the second catheter 170, as described in further detail herein.

The distal end portion 172 of the first catheter 170 extends beyond a distal end portion of the handle 110 and includes an occlusion member 178. The occlusion member 178 can be any suitable device or mechanism that is configured to selectively limit, block, obstruct, or otherwise occlude a lumen in which the occlusion member 178 is disposed. For example, in some embodiments, the occlusion member 178 can be substantially similar to the occlusion member 168 of the first catheter 160. In some embodiments, the arrangement of the second catheter 170 and the handle 110 can be such that the third port 130 and/or the fourth port 135 is in fluid communication with the occlusion member 178. Thus, in use, the third port 130 and/or the fourth port 135 can be fluidically coupled to a device that can supply a pressurized fluid (e.g., air, inert gas, or liquid) to the occlusion member 178 to transition the occlusion member 178 between a collapsed configuration and an expanded configuration, as described in further detail herein. In some embodiments, at least a portion of the occlusion member 178 can be selectively permeable to allow a biological agent to pass therethrough. Although not shown in FIGS. 2 and 3, in some embodiments, the distal end portion 172 of the second catheter 170 can define one or more openings. In such embodiments, the fifth port 140 can be fluidically coupled to a device that can supply irrigation, therapeutic material or agents, biological agents, and/or the like to a volume or region disposed between the occlusion member 168 of the first catheter 160 and the occlusion member 178 of the second catheter 170.

As described above, the actuator 150 of the device 100 can be operably coupled to the second set of ports 143. For example, in some embodiments, the actuator 150 is included in and/or coupled to the handle 110 and arranged relative to the second set of ports 143 to be operably coupled thereto. The actuator 150 can be any suitable device, mechanism, assembly, etc. that is movable between a first position relative to the handle 110, associated with the device 100 in the first configuration (FIG. 2), and a second position relative to the handle 110, associated with the device 100 in the second configuration (FIG. 3). Furthermore, with the actuator 150 operably coupled to the second set of ports 143, the actuator 150 can be operable in moving the second set of ports 143 between a first position relative to the handle 110 (e.g., the distal position) and a second position relative to the handle 110 (e.g., the proximal position), as indicated by the arrow AA in FIG. 3. Thus, when the second catheter 170 is coupled to the second set of ports 143, the actuator 150 can also move the second catheter 170 relative to the handle 110 and/or relative to the first catheter 160 as described in more detail below.

In some embodiments, the actuator 150 can be a push or pull slide that can move within a track (not shown in FIGS. 2 and 3) defined by the handle 110. In other embodiments, the actuator 150 can be coupled to an energy storage device (e.g., a spring, compressed gas, etc.) that is configured to move the actuator 150. For example, the actuator 150 can include a push button that allows a spring to transition from a compressed configuration towards an uncompressed configuration to move the actuator 150 relative to the handle 110. In other embodiments, a portion of the actuator 150 can be rotated to move the actuator 150 between its first position and its second position relative to the handle 110. With the second catheter 170 physically and fluidically coupled to the second set of ports 143 (as described above), the movement of the actuator 150 can move the second catheter 170 relative to the handle 110. More specifically, the proximal end portion 171 of the second catheter 170 can be movably disposed within the handle 110 (as described above) such that when the actuator 150 is moved from its first position to its second position, the proximal end portion 171 of the second catheter 170 is moved from a first position relative to the handle 110 (e.g., FIG. 2) to a second position relative to the handle 110 (e.g., FIG. 3).

With the second catheter 170 movably disposed about the first catheter 160, the movement of the actuator 150 moves the second catheter 170 relative to the first catheter 160. For example, when the device 100 is in the first configuration, a first distance D1 is defined between the occlusion member 168 of the first catheter 160 and the occlusion member 178 of the second catheter 170. Therefore, with the first catheter 160 fixedly disposed within the handle 110, the movement of the second catheter 170 in the proximal direction (e.g., the AA direction) increases the distance between the occlusion member 168 of the first catheter 160 and the occlusion member 178 of the second catheter 170 to a second distance D2, as shown in FIG. 3.

In use, a guidewire (not shown) can be inserted into the second port 125 and through a lumen defined by the first catheter 160. In this manner, the guidewire can be advanced through a bodily lumen and the device 100 can be manipulated to advance the first catheter 160 along the guidewire to place the distal end portion 162 of the first catheter 160 and the distal end portion 172 of the second catheter 170 at a target location within the bodily lumen. Once at the target location, the actuator 150 can be moved in the AA direction (e.g., the proximal direction) to define a desired distance between the occlusion member 168 of the first catheter 160 and the occlusion member 178 of the second catheter 170, thereby placing the device 100 in the second configuration (FIG. 3). As described above, an inflation source can be coupled to the second port 125 of the first catheter 160 and the same inflation source or a second inflation source can be coupled to the third port 130 and/or the fourth port 135 of the second catheter 170. With the desired distance defined between the occlusion members 168 and 178, the inflation source(s) can be used to inflate the occlusion members 168 and 178. Thus, the occlusion members 168 and 178 can be transitioned from the collapsed (e.g., deflated) configuration to the expanded (e.g., inflated) configuration to substantially isolate a segment of the bodily lumen disposed therebetween. With the occlusion members 168 and 178 substantially occluding the bodily lumen, a biological or therapeutic agent can be delivered to the substantially isolated segment via the fourth port 135. For example, the biological or therapeutic agent can be delivered through the fourth port 135 into a lumen of the second catheter that is in fluid communication with the opening (see, e.g., opening 479 in FIG. 20) defined by the distal end portion 172 of the second catheter 170. In some instances, the substantially isolated segment can be irrigated by coupling an irrigation source to the fifth port 140. Thus, the irrigation is delivered to the substantially isolated segment via the opening (described above) defined by the distal end portion 172 of the second catheter 170.

Figure 4:
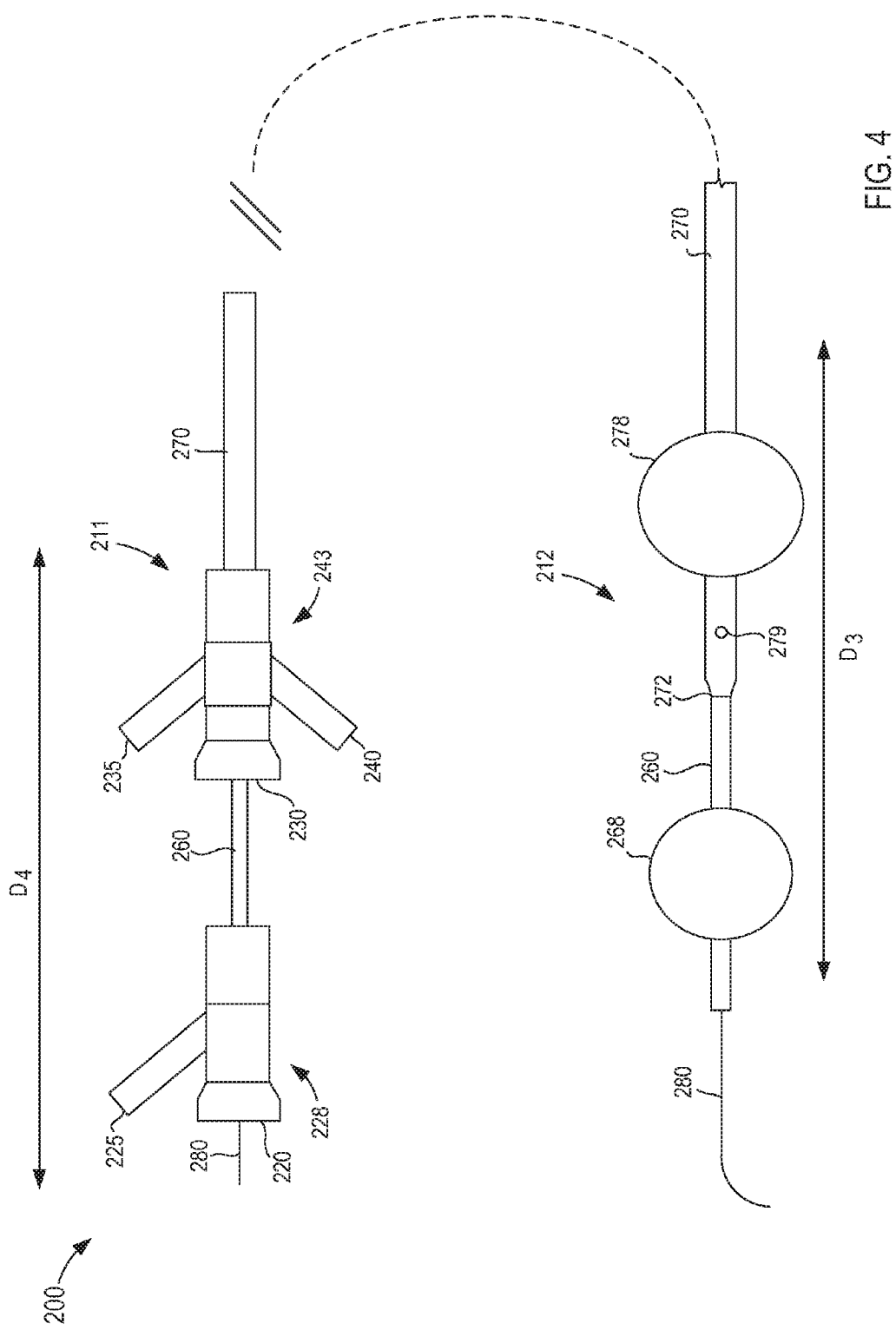
FIG. 4 is a side view of a multi-occlusion catheter insertion device according to an embodiment, shown in a dilated configuration.

FIGS. 4-11 illustrate a dilation catheter 200 according to an embodiment. FIG. 4 is a side view of the dilation catheter device 200 (also referred to herein as "catheter device"). In this embodiment, dilatation of two balloons is used to occlude a desired length of an artery such as, for example, the splenic artery 40 (see, e.g., FIG. 2). Specifically, the catheter device 200 includes a first catheter 260 (also referred to herein as "inner catheter") and a second catheter 270 (also referred to herein as "outer catheter"), a first Y-adaptor 228 (also referred to herein as "first set of ports") and a second Y-adaptor 243 (also referred to herein as "second set of ports"), a first occlusion element 268 (also referred to herein as "dilation element", "occluder," or "distal occlusion element"), and a second occlusion element 278 (also referred to herein as "dilation element", "occluder," or "proximal occlusion element") each configured to occlude a portion of an artery. The first occlusion element 268 is coupled to the first catheter 260 and the second occlusion element 278 is coupled to the second catheter 270.

The occlusion elements 268 and 278 can each be moved between a collapsed configuration (also referred to as "retracted configuration") for insertion of the catheter device 200 into a body of a patient (e.g., into an artery) and an expanded configuration (also referred to as "dilated configuration" or "inflated configuration") for occluding a portion of an artery. The occlusion elements 268 and 278 when in the collapsed configuration have a smaller outer perimeter (or diameter) than when in the expanded configuration.

The catheter device 200 includes a distal end portion 212 and a proximal end portion 211. In this embodiment, the occlusion elements 268 and 278 are expandable balloons coupled to an outer surface of the first catheter 260 and an outer surface of the second catheter 270, respectively, and are disposed at the distal end portion 212 of the catheter device 200. The catheter device 200 is shown in a dilated configuration in FIG. 4 with the occlusion elements 268 and 278 (i.e., balloons) in their expanded configuration (i.e., inflated, dilated).

Figure 5:
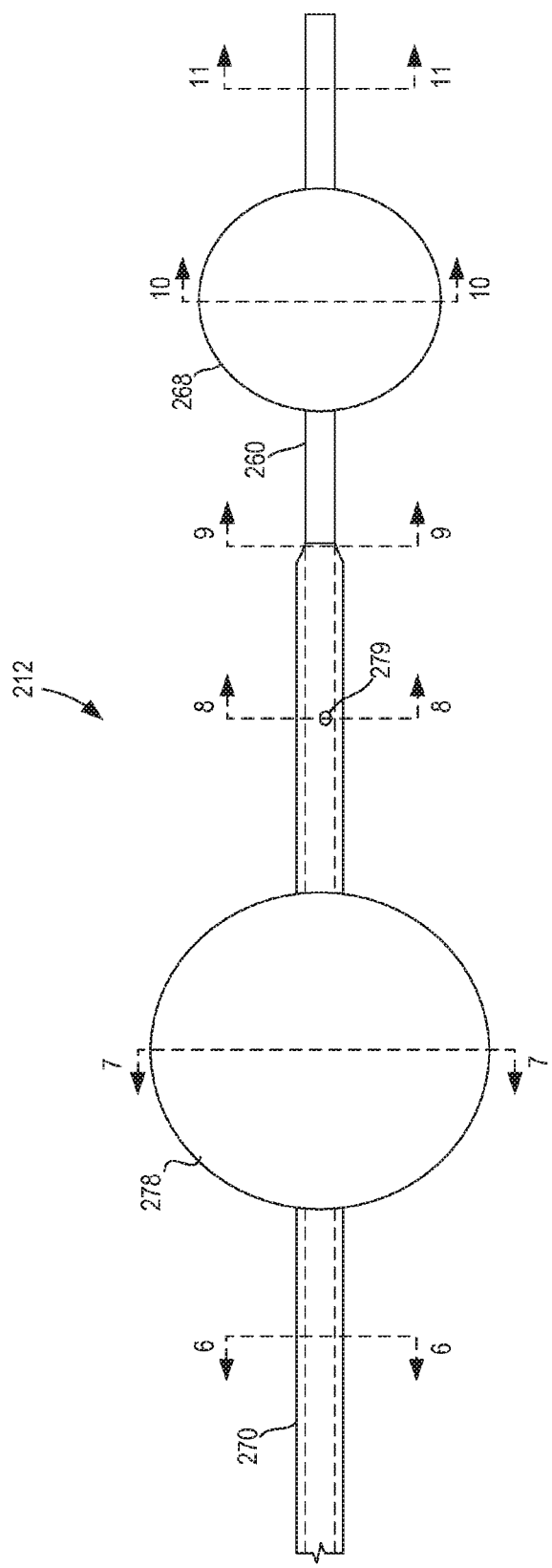
FIG. 5 is a side view of a portion of the multi-occlusion catheter insertion device of FIG. 4.
Figure 8:
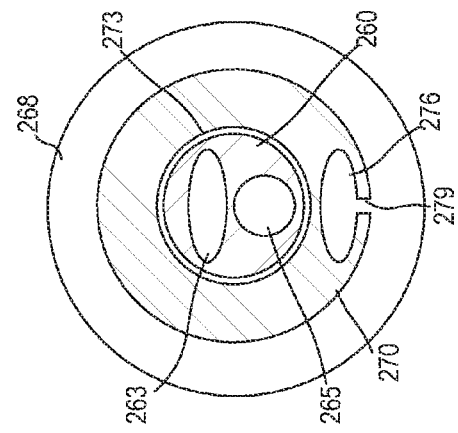
FIGS. 6-11 are each a cross-sectional view of a different portion of the multi-occlusion catheter insertion device of FIG. 4, taken along lines 6-6, 7-7, 8-8, 9-9, 10-10, and 11-11, respectively, in FIG. 5.

FIG. 5 is a side view of the distal end portion 212 of the catheter device 200 (e.g., a distal end portion of the first catheter 260 and the second catheter 270) and FIGS. 6-11 illustrate cross-sections at various locations along the distal end portion 212 of the catheter device 200 to illustrate the various lumens of the catheter device 200. As shown in FIGS. 6-11, the first catheter 260 defines a first lumen 265 and a second lumen 263 that each can extend a length of the first catheter 260. The first lumen 265 can be configured to receive a guidewire 280 (shown, for example, in FIG. 4). The second lumen 263 can be used to communicate an inflation medium to and from the first occlusion element 268 via an aperture 264 in fluid communication with the first occlusion element 268 (see, e.g., FIG. 10).

Figure 7:
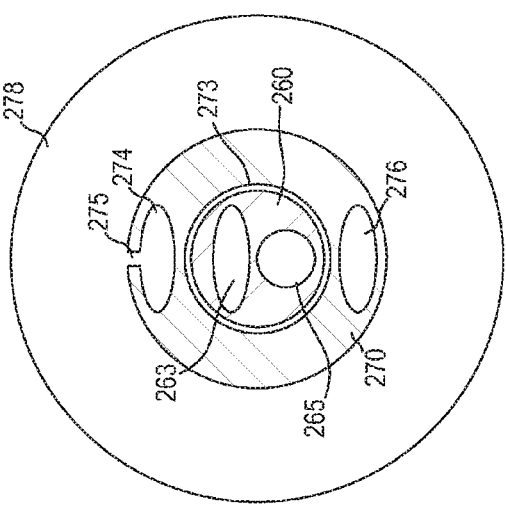
Figure 6:
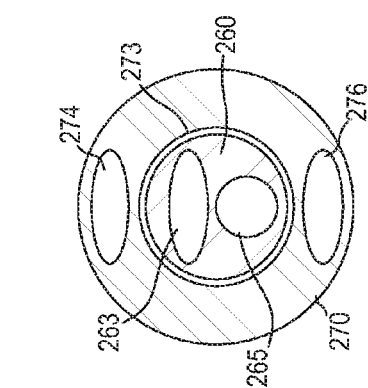
Figure 11:
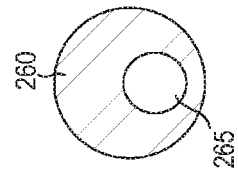
Figure 10:
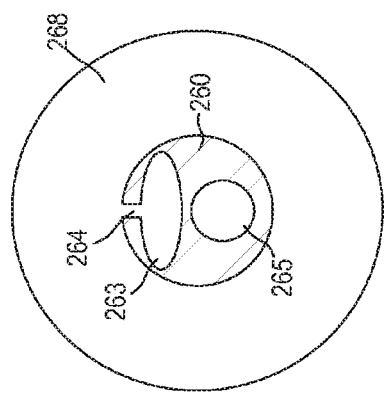
Figure 9:
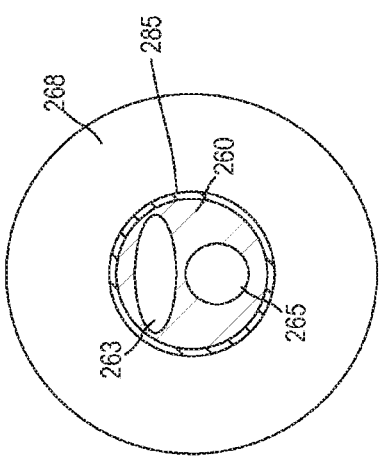

As shown, for example, in FIGS. 6 and 7, the second catheter 270 defines a first lumen 274, a second lumen 273, and a third lumen 276. The first lumen 274 can be used to communicate an inflation medium to and from the second occlusion element 278 via an aperture 275 in fluid communication with the second occlusion element 278 (see, e.g., FIG. 7). The second lumen 273 is configured to slidably receive at least a portion of the first catheter 260 therethrough, as shown in FIGS. 6-9. The third lumen 276 can terminate and be in fluid communication with an infusion aperture 279 near a distal end 272 of the second catheter 270 (see, e.g., FIG. 8). The infusion aperture 279 can be used to communicate a cell/biological/therapeutic material to a desired location within a body/artery of a patient.

The first Y-adaptor 228 is coupled to the first catheter 260 and includes two ports 220 and 225, as shown in FIG. 4. The port 220 defines a lumen (not shown) that is in fluid communication with the first lumen 263 of the catheter 260 and can be used to communicate an inflation medium to the first occlusion element 268 through the second lumen 263. For example, a source of an inflation medium (not shown) can be coupled to the catheter device 200 via the port 220 of the first Y-adaptor 228. The port 225 defines a lumen (not shown) that is in fluid communication with the second lumen 265 of the first catheter 260 (see, e.g., FIGS. 6-11) and can be used for introduction of the guidewire 280 into the second lumen 265.

The second Y-adapter 243 is coupled to the second catheter 270 and includes three ports 230, 235 and 240, as shown in FIG. 4. The port 230 defines a lumen (not shown) that is in fluid communication with the second lumen 273 of the second catheter 270 (see, e.g., FIGS. 6-11) and can receive the first catheter 260 therethrough. The port 235 defines a lumen (not shown) that is in fluid communication with the first lumen 274 of the second catheter 270 and can be used to communicate an inflation medium to and from the second occlusion element 278 in a similar manner as described above for port 225 and lumen 263. The port 240 defines a lumen (not shown) that is in fluid communication with the third lumen 276 of the second catheter 270 (see e.g., FIG. 6-11) and can be used to introduce cells/biological/therapeutic materials into and through the third lumen 276 and out through the infusion aperture 279.

The catheter device 200 can also include a seal element 285 (see, e.g., FIG. 9) (also referred to a as a "seal", "sealing element", "selective sealing element", or "filter-ring") disposed at or near a distal end 272 of the second catheter 270. The seal element 285 can prevent the entry of cells and or biologics that have been injected into an artery from flowing back into the lumen 273. By doing so, a maximum number of cells can be delivered to the treatment area, and improve engraftment efficiency. The seal element 285 can be for example, a ring, a membrane or other known sealing elements used in medical devices.

The slidable coupling of the first catheter 260 within the second lumen 273 of the second catheter 270 allows a collective length of the first catheter 260 and the second catheter 270 to be adjusted by slidably moving the first catheter 260 and the second catheter 270 relative to each other. Because the first occlusion element 268 is coupled to the first catheter 260 and the second occlusion element 278 is coupled to the second catheter 270, the slidable adjustment of the first catheter 260 and the second catheter 270 can thus allow adjustment of a distance between the second occlusion element 278 and the first occlusion element 268. The second lumen 273 of the second catheter 270 can be sized to receive the first catheter 260 with sufficient clearance to allow for ease of sliding/adjustment.

In use, the catheter device 200 can be placed at a desired location within an artery, such as for example, within a splenic artery 40 (see e.g., FIG. 1) and used to infuse a cell/biological material to a pancreas 30. A length of the first catheter 260 and the second catheter 270 can be adjusted such that a selected portion (e.g., a pancreatic portion) of the splenic artery 40 is isolated between the first occlusion element 268 and the second occlusion element 278. A cell/biologic material can be injected through the catheter device 200 and into the isolated region of the splenic artery 40.

The infusion of a cell/biological agent can occur in the localized region surrounding the isolated region or segment of vessel 40. In some instances, however, the presence of one or more additional, side-branching vessels forming a flow-restricting configuration in the isolated region of vessel 40 can allow infusion to occur in a larger semi-localized region. To allow the operator to accommodate the location of these side branches to fall within the isolated region, the first catheter 260 can be configured such that it is slidably associated with the second catheter 270 and the space between (e.g., distance between) occlusion elements 268 and 278 can be varied according to the circumstances of the desired treatment. The positioning of the distal occlusion element 268 within an artery can be individualized based on the specific anatomy to allow an enclosed or isolated area between the two occlusion elements 268 and 278 with a linear length ranging, for example, from 3 cm to 22 cm.

The cells targeted to the pancreas 30 (see e.g., FIG. 1) can be infused through infusion port 240, traverse through the third lumen 276, and exit through the infusion aperture 279 into the area isolated between the two occlusion elements 268 and 278. The catheter device 200 can be configured to enable delivery of target cells, such as insulin producing beta cells, and autologous stem cells (mesenchymal, bone marrow, and others) to blood vessels in communication with the pancreas in situ. The infusion pressure in the isolated blood vessel region can be measured with pressure monitoring through the infusion lumen of the catheter (with a monometer (not shown) in line with infusion port 279). The pressure in the third lumen 276 can be based on the size of the cells being delivered, on the flow rate, the viscosity of the solution, and/or flow resistance of the third lumen 276 of second catheter 270. The flow resistance of the catheter device 200 can in turn be determined based on, for example, the inner coating material, the size and the length of the third lumen 276, the size of the third port 240, and/or the size of the distal infusion aperture 279. The catheter device 200 can allow for rapid infusion of cells (e.g., up to 2 milliliter per second (ml/sec)). In some applications, the rapid infusion of cells can enhance uptake and eventual engraftment. Smaller aperture size (e.g., the infusion aperture 279), lumen size (e.g., the third lumen 276), and increased flow resistance may cause "sludging" of cells, leading to poor intra-arterial flow and diminished uptake. Lastly, the infusion aperture 279 and luminal design of the catheter device 200 can be configured to minimize risk of mechanical cell damage during the infusion process.

Figure 12:
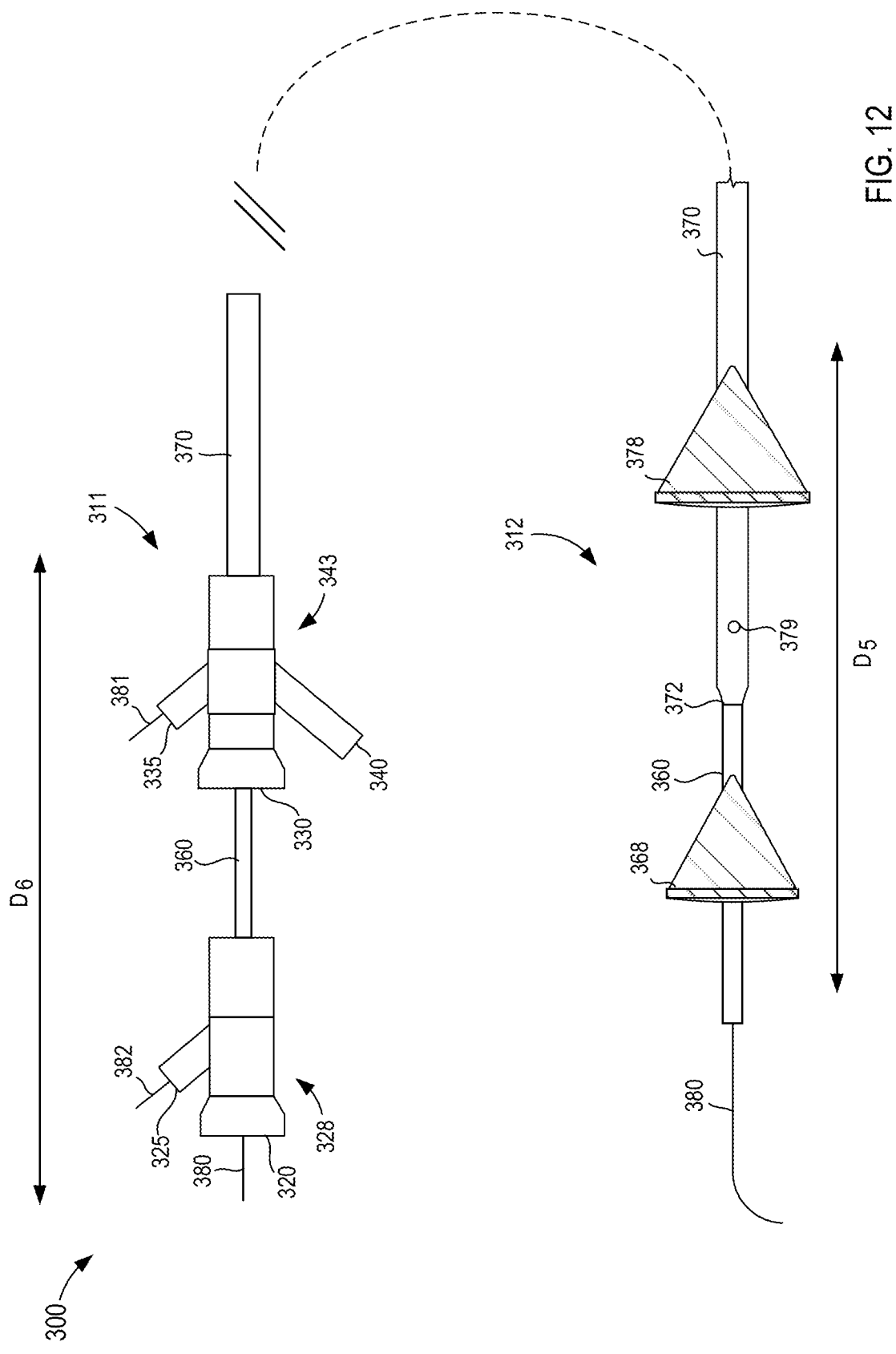
FIG. 12 is a side view of a multi-occlusion catheter insertion device according to an embodiment.

FIG. 12 illustrates an embodiment of a catheter device 300 that uses two filter elements, instead of expandable balloons to occlude and isolate the area of interest for infusion of cells or chemotherapeutic agents, without inhibiting the flow of plasma through the isolated area. The filter elements can be formed with, for example, a medical mesh material. The size of the pores of the filter elements can be, for example, about 2 microns (μm) or less in length, which can inhibit cells from passing through the filter element, but not impede serum/plasma and other components from passing through the filter element. The catheter device 300 can be used for the same or similar functions as described above for catheter device 200. For example, the catheter device 300 can be used for introduction of cells or other biologic or therapeutic material into a desired location within a patient's body, such as within a splenic artery.

The catheter device 300 includes a first catheter 360 and a second catheter 370 that can be slidably coupled together as described above for catheter device 200, a first Y-adaptor 328 (also referred to herein as "first set of ports") coupled to the first catheter 360, a second Y-adaptor 343 (also referred to herein as "second set of ports") coupled to the second catheter 370, a first occlusion element 368 (also referred to herein as "dilation element", "occluder", "distal occlusion element") and a second occlusion element 378 (also referred to herein as "dilation element", "occluder", "proximal occlusion element") to occlude a portion of an artery. The first occlusion element 368 is coupled to the first catheter 360 and the second occlusion element 378 is coupled to the second catheter 370.

In this embodiment, the occlusion elements 368 and 378 are filter elements that can be moved between a collapsed configuration (also referred to as "retracted configuration" or "closed configuration") for insertion of the catheter device 300 into a body of a patient (e.g., into an artery) and an expanded configuration (also referred to as "dilated configuration" or "open configuration"), as shown in FIG. 12, for occluding a portion of an artery. The occlusion elements 368 and 378 when in the collapsed configuration have a smaller outer perimeter (or diameter) than when in the expanded configuration.

Figure 13:
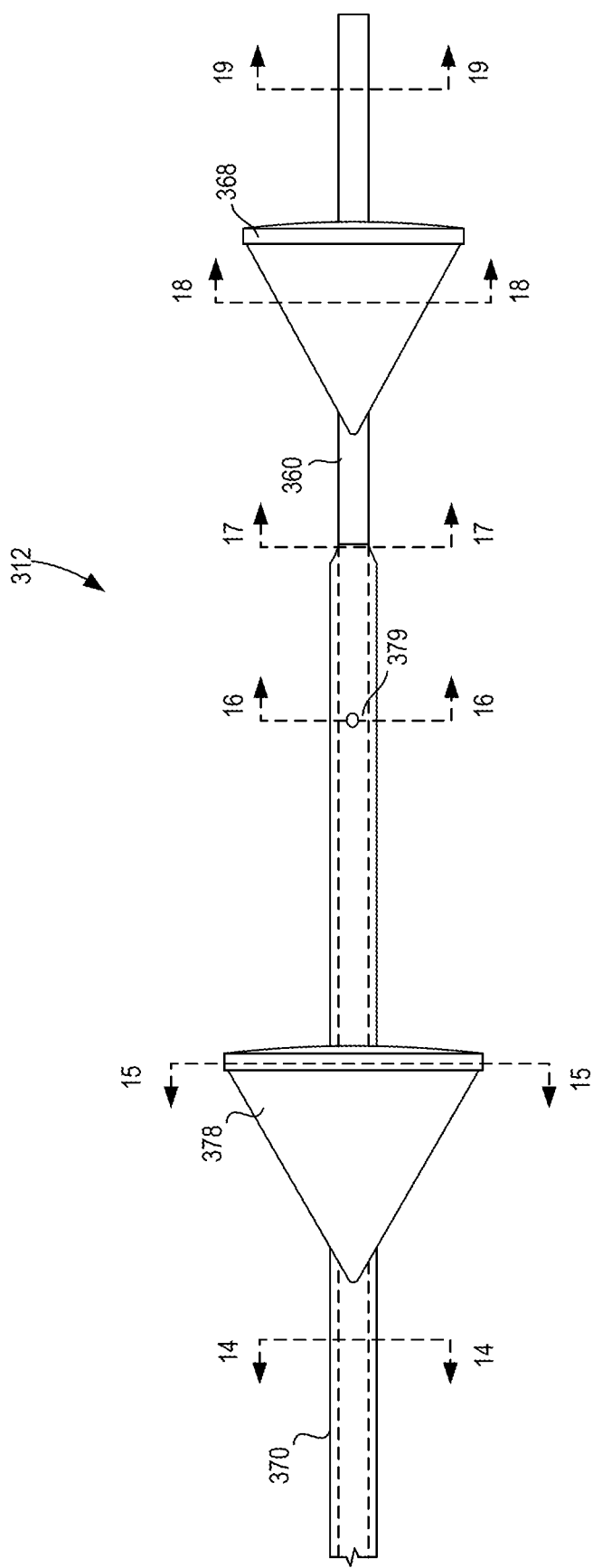
FIG. 13 is a side view of a portion of the multi-occlusion catheter insertion device of FIG. 12.

The catheter device 300 includes a distal end portion 312 and a proximal end portion 311. FIG. 13 is a side view of the distal end portion 312 of the catheter device 300 and FIGS. 14-19 illustrate cross-sections at various locations along the distal end portion 312 of the catheter device 300. As shown in FIGS. 14-19, the first catheter 360 defines a first lumen 363 and a second lumen 365 that each can extend a length of the first catheter 360. The first lumen 363 can be configured to receive a wire deployment device 382 that can be coupled to the filter element 368 and configured to move the filter element 368 from its expanded or open configuration and its collapsed or closed configuration. The second lumen 365 can be configured to receive a guidewire 380 (shown in FIG. 12).

The second catheter 370 defines a first lumen 373, a second lumen 374, and a third lumen 376. The first lumen 373 is configured to slidably receive at least a portion of the first catheter 360 therethrough. The second lumen 374 can be configured to receive a wire deployment device 381. The wire deployment device 381 can be coupled to the filter element 378 and used to move the filter element 378 between its expanded or open configuration and its collapsed or closed configuration. The third lumen 376 can terminate and be in fluid communication with an infusion aperture 379 (see, e.g., FIG. 16) near a distal end 372 of the second catheter 370. The infusion aperture 379 can be used to communicate, for example, a cell or cells (or other therapeutic or biologic material) to a desired location within a body of a patient.

The first Y-adaptor 328 includes a port 320 and a port 325 as shown in FIG. 12. The port 320 defines a lumen (not shown) that is in fluid communication with the first lumen 363 of the catheter 360. The port 325 defines a lumen (not shown) that is in fluid communication with the second lumen 365 of the catheter 360, and can be used for introduction of the guidewire 380 into the second lumen 365. The second Y-adapter 343 includes three ports 330, 335 and 340, as shown in FIG. 12. The port 330 defines a lumen (not shown) that is in fluid communication with the first lumen 373 of the second catheter 370 and can receive the first catheter 360 therethrough. The port 335 defines a lumen (not shown) that is in fluid communication with the second lumen 374 of the second catheter 370, and the port 335 defines a lumen (not shown) that is in fluid communication with the third lumen 376 of the second catheter 370.

The filter elements 368 and 378 can each be shaped as a cone when in their expanded or open configurations as shown in FIGS. 12 and 13. The filter elements 368 and 378 can each be sized when in their expanded or open configurations to meet the size of a particular vessel diameter in which the catheter device 300 is to be deployed. After infusion of cells or a therapeutic/biologic material through the catheter device 300, the filter elements 368 and 378 can be collapsed to a smaller size for removal of the catheter device 300 from the patient.

In some embodiments, a diameter of the occlusion elements (e.g., 268, 278, 368, and 378) when expanded within an artery, such as, for example, the splenic artery 40, can be adjustable to meet anatomical variations including a) individual variability in the size of the splenic artery 40 and b) end to end variation as the artery size can taper down between the two ends of the artery. As such, in some embodiments, to allow successful isolation of the area for treatment, the proximal occlusion element (e.g., the balloon 278 and/or the filter element 378) can be sized (e.g., have an outer diameter or outer perimeter) between, for example, 3-12 mm and the distal occlusion element (e.g., the balloon 268 and/or the filter element 368) between, for example, 3-12 mm. The proximal occlusion element can be larger than the distal occlusion element, smaller than the distal occlusion element, or the same size as the distal occlusion element.

Referring now to FIGS. 20-29, a multi-lumen catheter insertion device 400 is illustrated according to an embodiment. The multi-occlusion catheter insertion device 400 (also referred to herein as "catheter device" or "device") includes a handle 410, an actuator 450, a first catheter 460 (also referred to herein as "inner catheter"), and a second catheter 470 (also referred to herein as "outer catheter") and can be movable between a first configuration and a second configuration. As described in further detail herein, the device 400 can be grasped by a user (e.g., a doctor, physician, surgeon, technician, etc.) and manipulated substantially single handedly to insert a portion of the first catheter 460 and a portion of the second catheter 470 into a bodily lumen of a patient and to move, inflate, deflate, adjust, and/or otherwise reconfigure the portion of the first catheter 460 and the portion of the second catheter 470 within the bodily lumen. For example, the second catheter 470 can be moved relative to the first catheter 460, and vice-versa, to adjust a distance between a first occlusion element 468 coupled to a distal end portion of the first catheter 460 and a second occlusion element 478 coupled to a distal end portion of the second catheter 470. The device 400 can be used to isolate a segment of a bodily lumen within the space or region defined between the first occlusion element 468 and the second occlusion element 478. Thus, a procedure can then be performed within the isolated segment such as, for example, delivering a cell or a therapeutic/biological agent to the isolated segment.

The handle 410 of the device 400 can be any suitable shape, size, or configuration. For example, in some embodiments, the handle 410 can have a shape and size that can enhance the ergonomics of the device 400. More specifically, the handle 410 has a proximal end portion 411, a distal end portion 412, and a medial portion 413 that can be shaped in such a manner as to be easily gripped by a user (e.g., a doctor, physician, surgeon, technician, etc.). In some embodiments, the handle 410 can include a grip section 417 (see, e.g., FIG. 21) or the like that can have, for example, a rough surface finish, detents, protrusions, or the like that can enhance the ergonomics of the handle 410. In other embodiments, the grip section can be, for example, an insert, an over-mold, or the like that is formed from a relatively deformable material and that can have a relatively high coefficient of friction, thereby enhancing the ergonomics of the handle 410.

The proximal end portion 411 of the handle 410 includes a first port 420 and a second port 425 collectively referred to herein as a first set of ports 428). The first port 420 and the second port 425 can be any suitable size, shape, or configuration. In some embodiments, the first port 420 and the second port 425 can be coupled together via any suitable method (e.g., an adhesive, ultrasonic welding, mechanical fastener, and/or the like). In other embodiments, the first port 420 and the second port 425 can be monolithically formed.

Figure 20:
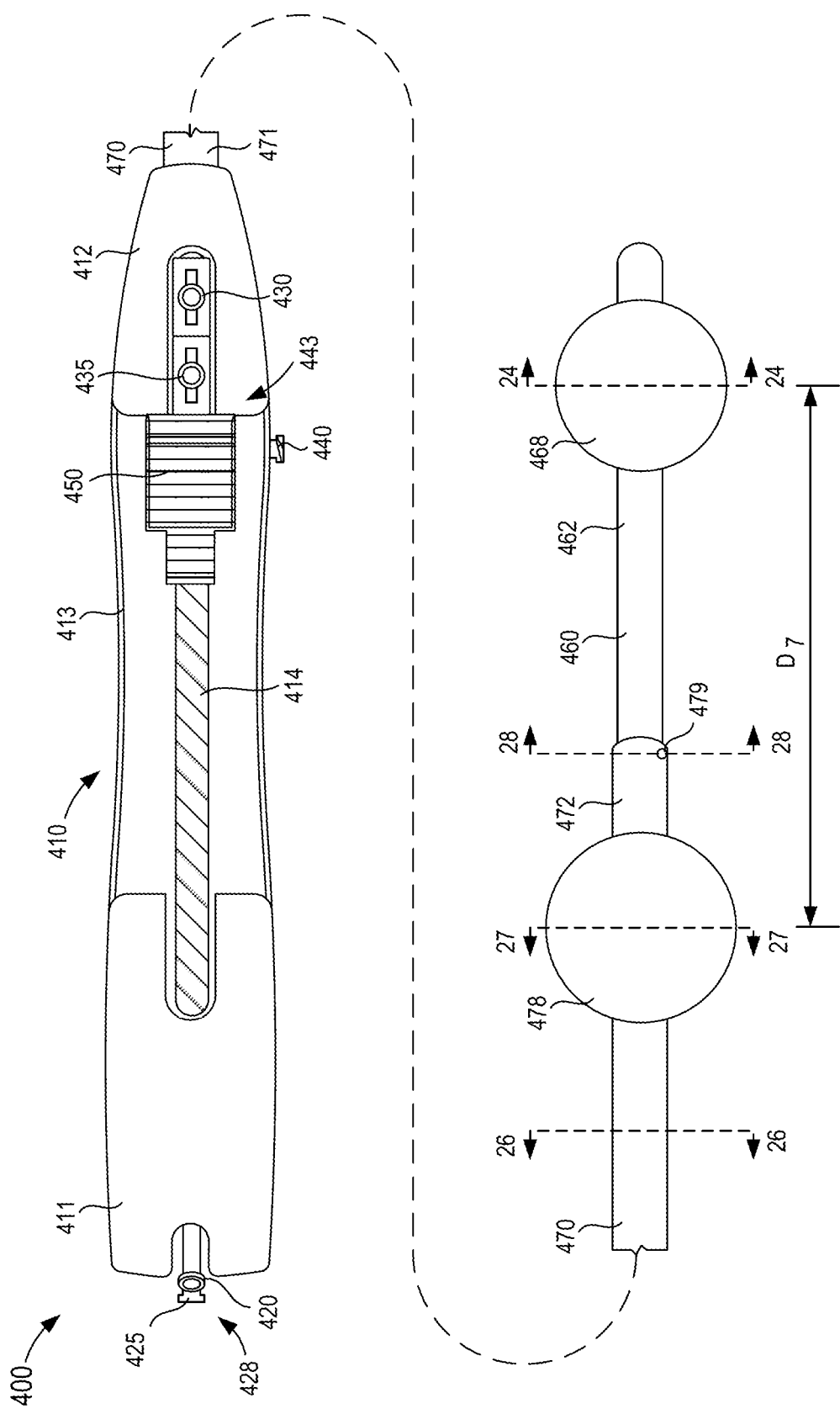
FIG. 20 is a top view of a multi-occlusion catheter insertion device according to an embodiment, in a first configuration.

The first port 420 and the second port 425 can extend from the proximal end portion 411 of the handle 410 such that at least a portion of the first port 420 and the second port 425 is accessible, as shown in FIGS. 20 and 21. In some embodiments, the first set of ports 428 can be, for example, a first Y-adapter, substantially similar to the Y-adapter 228 and/or 328. In other embodiments, a first port and a second port can be, for example, substantially parallel in a stacked configuration. In yet other embodiments, a handle can include a first port and a second port that are substantially coaxial and arranged in a substantially concentric configuration such that at least a portion of the first port is disposed within the second port, or vice versa.

Although not shown in FIGS. 14-29, the first port 420 and the second port 425 can be physically and fluidically coupled to an exterior device, mechanism, and/or the like as described above, for example, with reference to insertion device 100. For example, the first port 420 and the second port 425 can each define a lumen (described in more detail below) in fluid communication with such a device. The first port 420 and the second port 425 can each include a Luer-Lok® and/or any other attachment mechanism that can physically and fluidically couple the first port 420 and/or the second port 425 to any suitable device either directly or indirectly (e.g., by an intervening structure such as a flexible tubing to the like). The first set of ports 428 can be physically and fluidically coupled to the first catheter 460 such that when an external device is coupled to the handle 410 via the first port 420 and/or the second port 425, at least the portion of the first catheter 460 is placed in fluid communication with that external device via the first port 420 and/or the second port 425. For example, the first port 420 can be coupled to a device that can, for example, supply a pressurized fluid (e.g., an inert gas, air, saline, water, and/or any other suitable fluid in gaseous or liquid form) that can flow through the first port 420 to be delivered to a portion of the first catheter 460, as described in further detail herein. Furthermore, the second port 425 can be coupled to a device that can advance a guidewire or the like through the second port 425 and into a portion of the first catheter 460, as described in further detail herein. In some embodiments, a guidewire or the like can be manually inserted through the second port 425 without the use of an external device.

The distal end portion 412 of the handle 410 includes a third port 430, a fourth port 435, and a fifth port 440 (collectively referred to as a second set of ports 443). In some embodiments, the second set of ports 443 includes the fifth port 440 and only one of the third port 430 and the second port 435. The second set of ports 443 can be any suitable size, shape, or configuration as described above with reference to the first set of ports 428. For example, the second set of ports 443 can be, for example, monolithically and/or unitarily formed. In some embodiments, the second set of ports 443 can be monolithically formed with the catheter 470. In some embodiments, the second set of ports 443 can be formed with and/or coupled to any suitable structure or component of the handle 410 such that the second set of ports 443 can be moved relative to the handle 410 as described in more detail below.

The third port 430, the fourth port 435, and the fifth port 440 can each include a Luer-Lok® and/or any other attachment mechanism that can physically and fluidically couple the third port 430, the fourth port 435, and/or the fifth port 440 to any suitable attachment, device, mechanism, and/or the like. The second set of ports 443 can be physically and fluidically coupled to the second catheter 470 such that when an external device is coupled to the handle 410 via the third port 430, the fourth port 435, and/or the fifth port 440, at least a portion of the second catheter 470 is placed in fluid communication with that external device. For example, in some embodiments, the third port 430 and/or the fourth port 435 can be coupled to a device that can supply a pressurized fluid (as described above) that can flow through the third port 430 and/or the fourth port 435, respectively, to be delivered to a portion of the second catheter 470, as described in further detail herein. In some embodiments, the fifth port 440 is coupled to, for example, an infusion device that is configured to deliver a biological or therapeutic agent and/or other suitable drug formulation to a target tissue via the fifth port 440 and a portion of the second catheter 470. In some embodiments, the fifth port 440 can be coupled to, for example, an irrigation device that can deliver an irrigation fluid to, for example, an isolated segment of a bodily lumen via the fifth port 440 and a portion of the second catheter 470. In some embodiments, the fifth port 440 can be coupled to, for example, the infusion device configured to deliver the biological agent and/or other suitable drug formulation, as described in further detail herein.

As shown in FIGS. 20-22, the handle 410 defines a first track 414 and a second track 416. The first track 414 slidably receives a portion of the actuator 450. More specifically, at least a portion of the actuator 450 can extend through the track 414, thereby allowing a user to engage the actuator 450. As such, the track 414 can define a path along which the actuator 450 can be moved between a first position relative to the handle 410 and a second position relative to the handle 410, as described in further detail herein. In a similar manner, the second track 416 slidably receives a portion of the fifth port 440. In this manner, the fifth port 440 can extend through the second track 416 to be accessed by a user. Moreover, the second track 416 can define a path along which the fifth port 440 can be moved, as described in further detail herein.

Although the device 400 is particularly shown in FIGS. 20-29, the arrangement of the first set of ports 428, the second set of ports 443, the first track 414 and the second track 416 can be arranged along a surface of the handle 410 in various orientations. For example, although the first track 414 is shown as being defined by a top surface of the handle 410 (see, e.g., FIG. 20) and the second track 416 as being defined by a side surface of the handle 410 (see, e.g., FIG. 21), in other embodiments, a first track configured to receive an actuator can be defined by a side surface of a handle and a second track configured to receive a fifth port can be defined by a top surface of the handle. Similarly, while the first set of ports 428 and the second set of ports 443 are shown extending from the handle 410 in a specific orientation, the first set of ports 428 and/or the second set of ports 443 can be oriented in any suitable manner relative to a surface of the handle 410.

Figure 29:
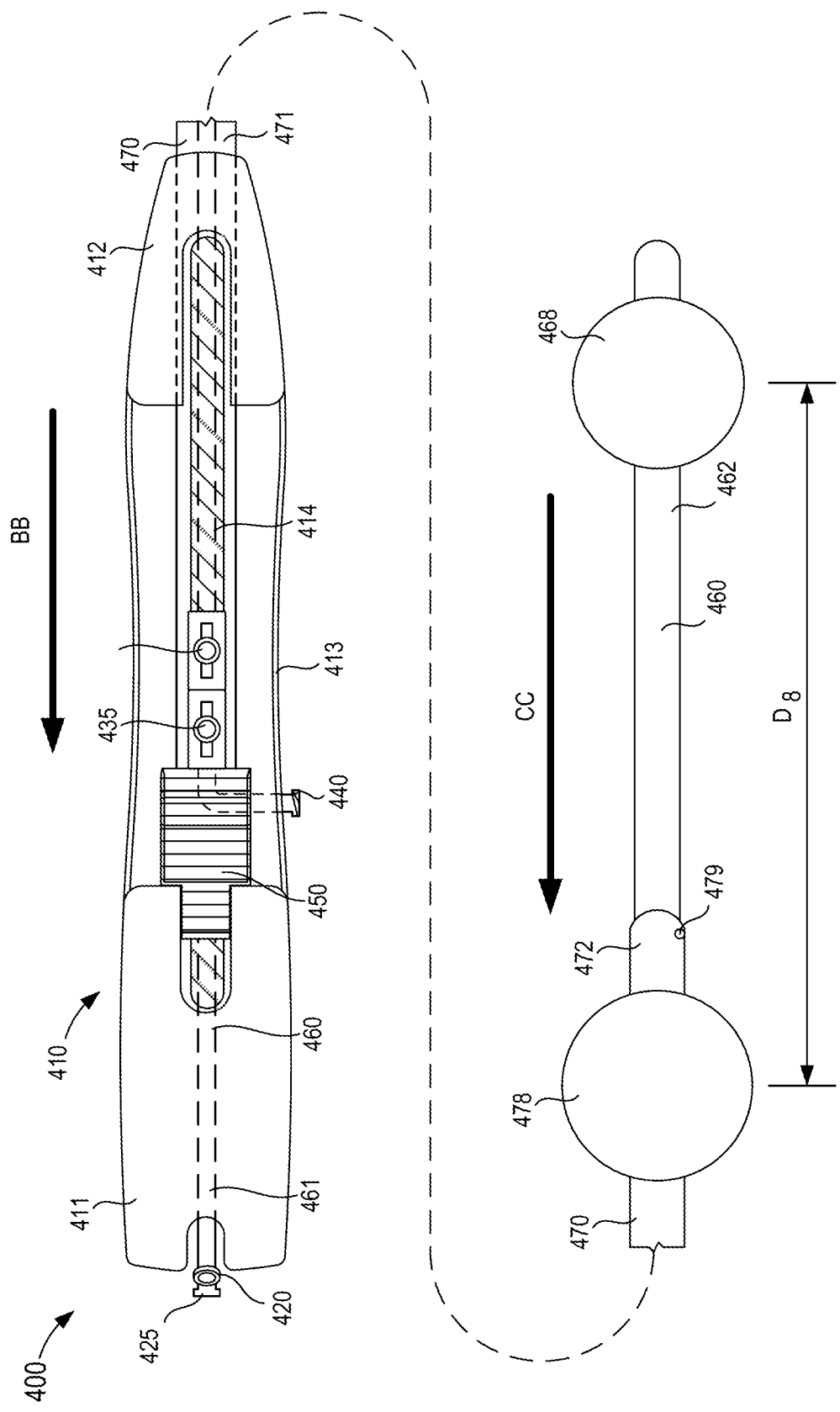
FIG. 29 is a top view of the multi-occlusion catheter insertion device of FIG. 20 in a second configuration.

The actuator 450 of the device 400 is operably coupled to the second set of ports 443. For example, in some embodiments, the actuator 450 is included in and/or coupled to the handle 410 and arranged relative to the second set of ports 443 to be operably coupled thereto. In other embodiments, a handle can be arranged such that at least a portion of an actuator is monolithically formed with at least a portion of a second set of ports. In some embodiments, an actuator is operably coupled to a second set of ports via an intervening structure or the like. For example, in some embodiments, the second set of ports 443 can be coupled to a shuttle or the like, which in turn, is coupled to an actuator. The actuator 450 can be any suitable device, mechanism, assembly, etc. that is movable between the first position relative to the handle 410, associated with the device 400 in the first configuration (FIGS. 20-22), and a second position relative to the handle 410, associated with the device 400 in the second configuration (FIG. 29).

In some embodiments, the actuator 450 can be a mechanism that can be pushed or pulled to slide within the first track 414 defined by the handle 410 between its first position and its second position. In some embodiments, the actuator 450 can be arranged to slide relatively smoothly within the track 414 when moved between its first position and its second position. In other embodiments, the handle 410 and/or the actuator 450 can include a set of ribs, teeth, detents, protrusions, etc. that are sequentially engaged as the actuator 450 is moved between its first position relative to the handle 410 and its second position relative to the handle 410. In this manner, a user can move the actuator 450 a desired distance that can be quantified by the actuator 450 and/or the handle 410 engaging a particular surface (e.g., a particular rib, tooth, detent, protrusion, etc.). In some embodiments, the handle 410 and/or the actuator 450 can be arranged at a predetermined setting that can correspond to a predetermined distance (e.g., 2 cm, 3 cm, etc.) between an end portion of the first catheter 460 and an end portion of the second catheter 470. In some embodiments, the set of ribs, teeth, detents, protrusions, etc. included in the handle 410 and/or the actuator 450 can be associated with pre-defined settings and/or adjustments.

Although not shown in FIGS. 20-29, in some embodiments, a handle 410 can include a visual indicator such as a measuring scale or the like. For example, in some embodiments, the handle 410 can include indicia (e.g., lines, markings, tic marks, etc.) that represents a gradation of a length of travel associated with moving the actuator 450 between its first position relative to the handle 410 and its second position relative to the handle 410. In some embodiments, the markings can represent distances of, for example, a centimeter, half a centimeter, a millimeter, and/or the like. In this manner, a user can view the indicia to determine a desired distance to move that actuator 450 that would otherwise be challenging or indeterminate. In some embodiments, the visual indicator can substantially correspond with the ribs, teeth, detents, protrusions, etc. of the handle 410 and/or actuator 450.

In some embodiments, the actuator 450 can be operably coupled to one or more energy storage device (e.g., a spring or the like) that can facilitate the movement of the actuator 450. For example, the actuator 450 can include a push button that can rearrange or reconfigure at least a portion of the actuator 450 to allow a spring to transition from a compressed configuration towards an uncompressed configuration to move the actuator 450 relative to the handle 410.

With the actuator 450 coupled to or monolithically formed with a portion of the second set of ports 443, the actuator 450 can be operable in moving the second set of ports 443 between a first position relative to the handle 410 (e.g., a distal position) and a second position relative to the handle 410 (e.g., a proximal position). Moreover, with the second catheter 470 physically and fluidically coupled to the second set of ports 443 (as described above), the movement of the actuator 450 and the second set of ports 443 can move the second catheter 470 between a first position relative to the handle 410 and a second position relative to the handle 410, as described in further detail herein.

Figure 23:
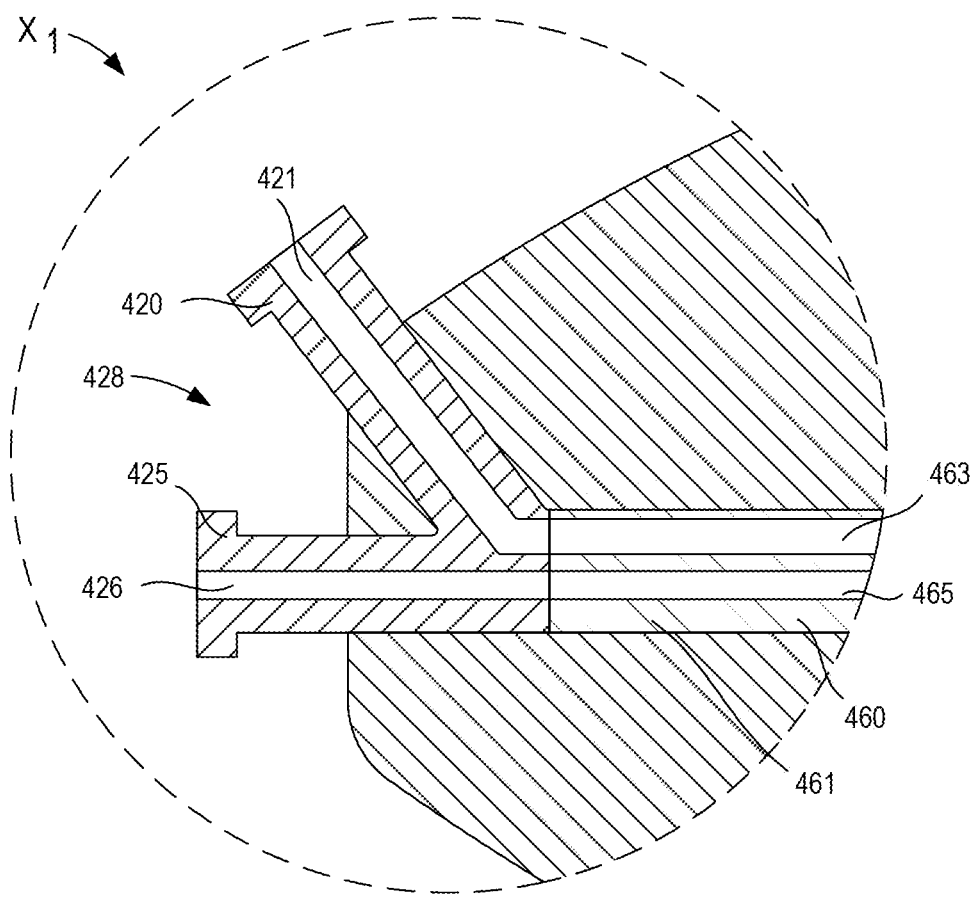
FIG. 23 is an enlarged cross-sectional view of a portion of the handle of FIG. 21, indicated by the region X1 and taken along the line 23-23 in FIG. 22.

The first catheter 460 and the second catheter 470 can be any suitable catheter device. For example, in some embodiments, the first catheter 460 and the second catheter 470 are multi-lumen catheters. The first catheter 460 has a proximal end portion 461 (see, e.g., FIGS. 21, 23 and 29) and a distal end portion 462 (see, e.g., FIGS. 20 and 29), and defines a first lumen 463 and a second lumen 465 (see, e.g., FIGS. 24-28). The proximal end portion 461 of the first catheter 460 is disposed within a portion of the handle 410. More specifically, the proximal end portion 461 of the first catheter 460 can be fixedly disposed within the portion of the handle 410 to place the first catheter 460 in fluid communication with the first set of ports 428. In some embodiments, the first catheter 460 can be physically and fluidically coupled to the first set of ports 428. In other embodiments, a device can include a first catheter that is monolithically formed with a first set of ports. In this manner, the proximal end portion 461 of the first catheter 460 is arranged such that the first lumen 463 of the first catheter 460 is in fluid communication with a lumen 421 defined by the first port 420 and the second lumen 465 of the first catheter 460 is in fluid communication with a lumen 426 of the second port 425, as shown in FIG. 23. Therefore, an external device (e.g., a device that can supply a pressurized fluid, as described above) can be physically and fluidically coupled to the first port 420 to place the external device in fluid communication with the first lumen 463 of the first catheter 460. Similarly, an external device including at least a guidewire (not shown) can be coupled to the second port 425 and can be manipulated to advance the guidewire through the second port 425 and into the second lumen 465, as described in further detail herein.

Referring back to FIG. 20, the distal end portion 462 of the first catheter 460 extends beyond a distal end portion of the handle 410 and includes an occlusion member 468. The occlusion member 468 can be any suitable device or mechanism that is configured to selectively limit, block, obstruct, or otherwise occlude a body lumen (e.g., artery) in which the occlusion member 468 is disposed. For example, in some embodiments, the occlusion member 468 can be an inflatable balloon or the like that can be transitioned between a collapsed (e.g., deflated) configuration and an expanded (e.g., inflated) configuration.

Figure 24:
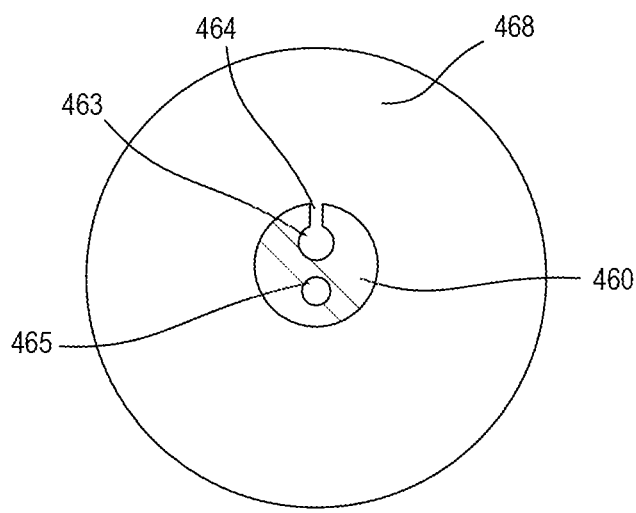
FIG. 24 is a cross-sectional view of a portion of the multi-occlusion catheter insertion device of FIG. 20, taken along the line 24-24.

The arrangement of the first catheter 460 can be such that the first lumen 463 is in fluid communication with the occlusion member 468. For example, as shown in FIG. 24, the distal end portion 462 of the first catheter 460 can define a channel 464 that places the first lumen 463 in fluid communication with the occlusion member 468. Thus, when the first port 420 is fluidically coupled to a device that supplies a pressurized fluid (e.g., air, inert gas, or liquid), the pressurized fluid can be delivered to the occlusion member 468 via the lumen 421 of the first port 420, the first lumen 463 of the first catheter 460, and the channel 464 of the first catheter 460. In this manner, the pressurized fluid can transition the occlusion member 468 between a collapsed configuration (not shown) and an expanded configuration (see e.g., FIG. 20), as described in further detail herein.

The second catheter 470 of the device 400 has a proximal end portion 471 (see, e.g., FIGS. 20-22) and a distal end portion 472 (see, e.g., FIGS. 20 and 29), and defines a first lumen 473, a second lumen 474, a third lumen 476 and an opening 479 (also referred to herein as "infusion aperture") (as shown, for example, in FIGS. 25-28). The second catheter 470 is movably disposed about a portion of the first catheter 460 (see, e.g., FIGS. 21-23). More specifically, the second catheter 470 can be arranged such that the first catheter 460 is movably disposed within the first lumen 473 defined by the second catheter 470, as shown, for example, in FIGS. 26-28.

Figure 25:
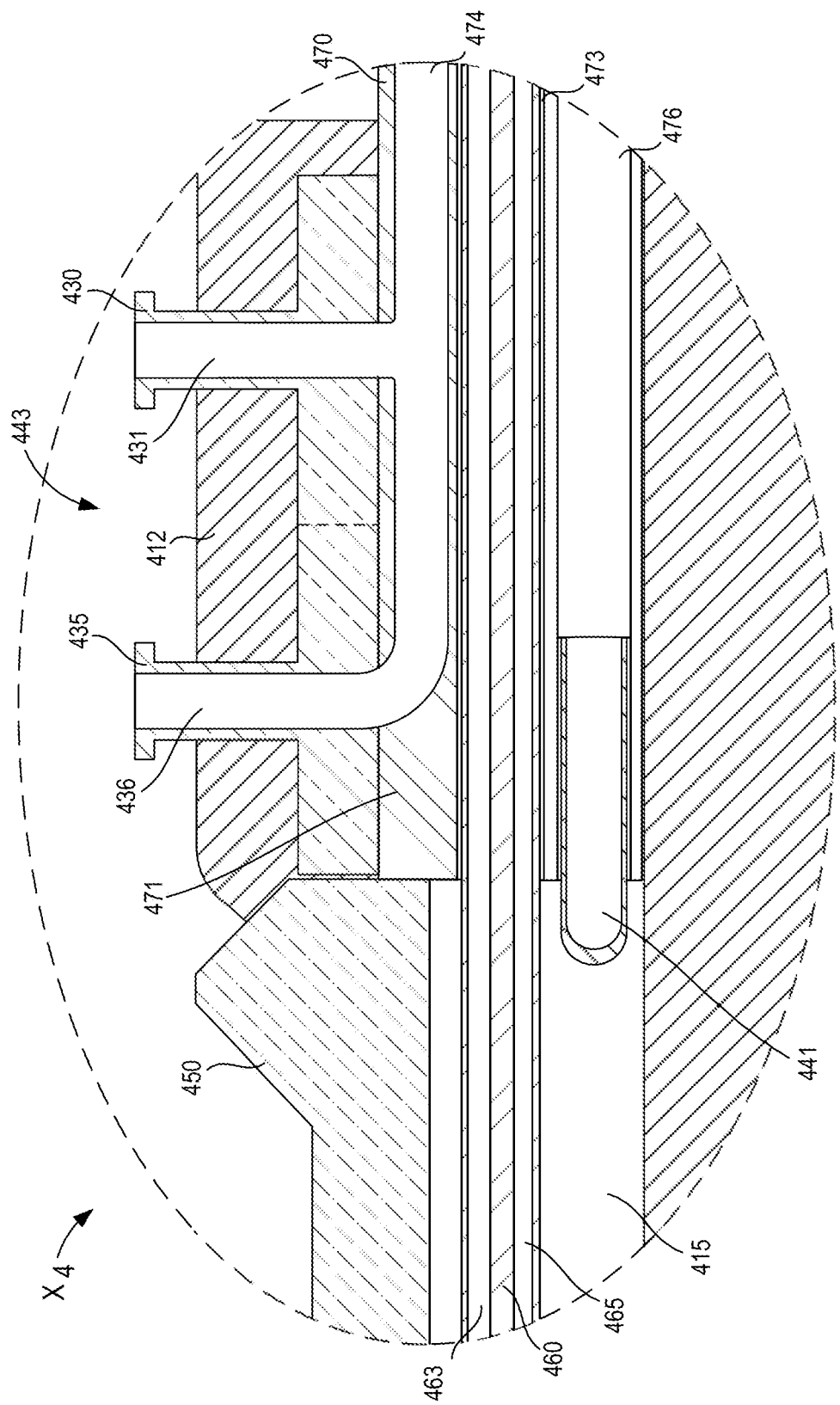
FIG. 25 is an enlarged cross-sectional view of a portion of the handle of FIG. 21, indicated by the region X2 and taken along the line 25-25 in FIG. 22.
Figure 26:
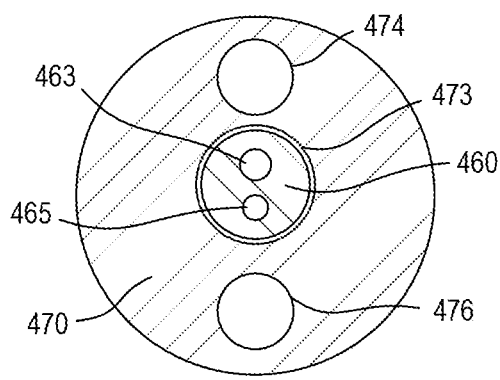
FIG. 26 is a cross-sectional view of a portion of the multi-occlusion catheter insertion device of FIG. 20, taken along the line 26-26.

The proximal end portion 471 of the second catheter 470 is movably disposed within the handle 410 to place the second catheter 470 in fluid communication with the second set of ports 443. In some embodiments, the second catheter 470 can be physically and fluidically coupled to the third port 430 and the fourth port 435, and/or the fifth port 440. In other embodiments, a catheter insertion device can include a second catheter that can be movably disposed within a handle and can be operably coupled to one or more ports via an intervening structure such as, for example, flexible tubing or the like. In yet other embodiments, a catheter insertion device can include a second catheter that is monolithically formed with a third port, a fourth port, and/or a fifth port. In this manner, the second catheter 470 is arranged such that the first lumen 473 of the second catheter 470 movably receives the first catheter 460, the second lumen 474 of the second catheter 470 is in fluid communication with a lumen 431 defined by the third port 430 and a lumen 436 defined by the fourth port 435, and the third lumen 476 of the second catheter 470 is in fluid communication with a lumen 441 defined by the fifth port 440, as shown in FIG. 25.

Referring back to FIG. 20, the distal end portion 472 of the first catheter 470 extends beyond a distal end portion of the handle 410 such that an occlusion member 478 of the second catheter 470 is disposed in a proximal position relative to the occlusion member 468 of the first catheter 478. Expanding further, the first catheter 460 extends within the proximal end portion 471 and the distal end portion 472 when disposed in the first lumen 473. Thus, the occlusion member 468 of the first catheter 460 can be disposed in a distal position relative to the occlusion member 478 of the second catheter 470. The occlusion member 478 can be any suitable device or mechanism that is configured to selectively limit, block, obstruct, or otherwise occlude a body lumen (e.g., artery) in which the occlusion member 478 is disposed. For example, in some embodiments, the occlusion member 478 can be substantially similar to the occlusion member 468 of the first catheter 468.

Figure 27:
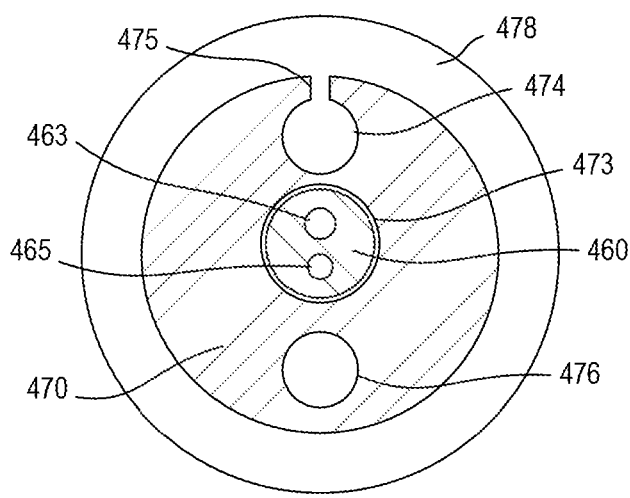
FIG. 27 is a cross-sectional view of a portion of the multi-occlusion catheter insertion device of FIG. 20, taken along the line 27-27.
Figure 28:
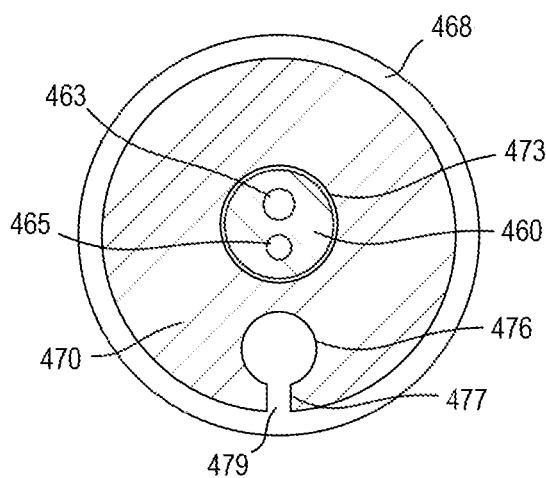
FIG. 28 is a cross-sectional view of a portion of the multi-occlusion catheter insertion device of FIG. 20, taken along the line 28-28.

The arrangement of the second catheter 470 can be such that the second lumen 474 is in fluid communication with the occlusion member 468. For example, as shown in FIG. 27, the distal end portion 472 of the second catheter 470 defines a channel 475 that places the second lumen 474 in fluid communication with the occlusion member 478. Thus, when the third port 430 (and/or the fourth port 435) is fluidically coupled to a device that supplies a pressurized fluid, the pressurized fluid can be delivered to the occlusion member 478 via the lumen 431 of the third port 430 (and/or the lumen 436 of the fourth port 435), the second lumen 474 of the second catheter 470, and the channel 475 of the second catheter 470. In this manner, the pressurized fluid can transition the occlusion member 478 between a collapsed configuration (not shown) and an expanded configuration (as shown in FIGS. 20 and 29). In a similar manner, the arrangement of the second catheter 470 can be such that the third lumen 476 is in fluid communication with the opening 479 (see, e.g., FIG. 28). For example, the distal end portion 472 of the second catheter 470 defines a channel 477 that places the third lumen 476 in fluid communication with the opening 479, as shown in FIG. 28. Thus, when the fifth port 440 is fluidically coupled to an external device that supplies irrigation or to a device that supplies a therapeutic agent, the irrigation fluid or therapeutic agent can be delivered to an isolated segment of a bodily lumen via the lumen 441 defined by the fifth port 440 and the third lumen 476, the channel 477, and the opening 479 defined by the second catheter 470.

The device 400 can be moved from the first configuration to the second configuration by moving the actuator 450 from its first position (e.g., a distal position) relative to the handle 410 to its second position (e.g., a proximal position) relative to the handle 410, as indicated by the arrow BB in FIG. 29. Expanding further, with the second catheter 470 movably disposed about the first catheter 460 and with the proximal end portion 471 of the second catheter 470 operably coupled to the actuator 450, the movement of the actuator 450 from its first position to its second position moves the second catheter 470 relative to the first catheter 460, as indicated by the arrow CC in FIG. 29. For example, when the device 400 is in the first configuration, a first distance D7 (FIG. 20) can be defined between the occlusion member 468 of the first catheter 460 and the occlusion member 478 of the second catheter 470. With the first catheter 460 fixedly disposed within the handle 410, the movement of the second catheter 470 in the CC direction (e.g., the proximal direction) increases the distance between the occlusion member 468 of the first catheter 460 and the occlusion member 478 of the second catheter 470 to a second distance D8, as shown in FIG. 29. Thus, a segment or volume having a desired length can be defined between the occlusion member 468 of the first catheter 460 and the occlusion member 478 of the second catheter 470.

Figure 30:
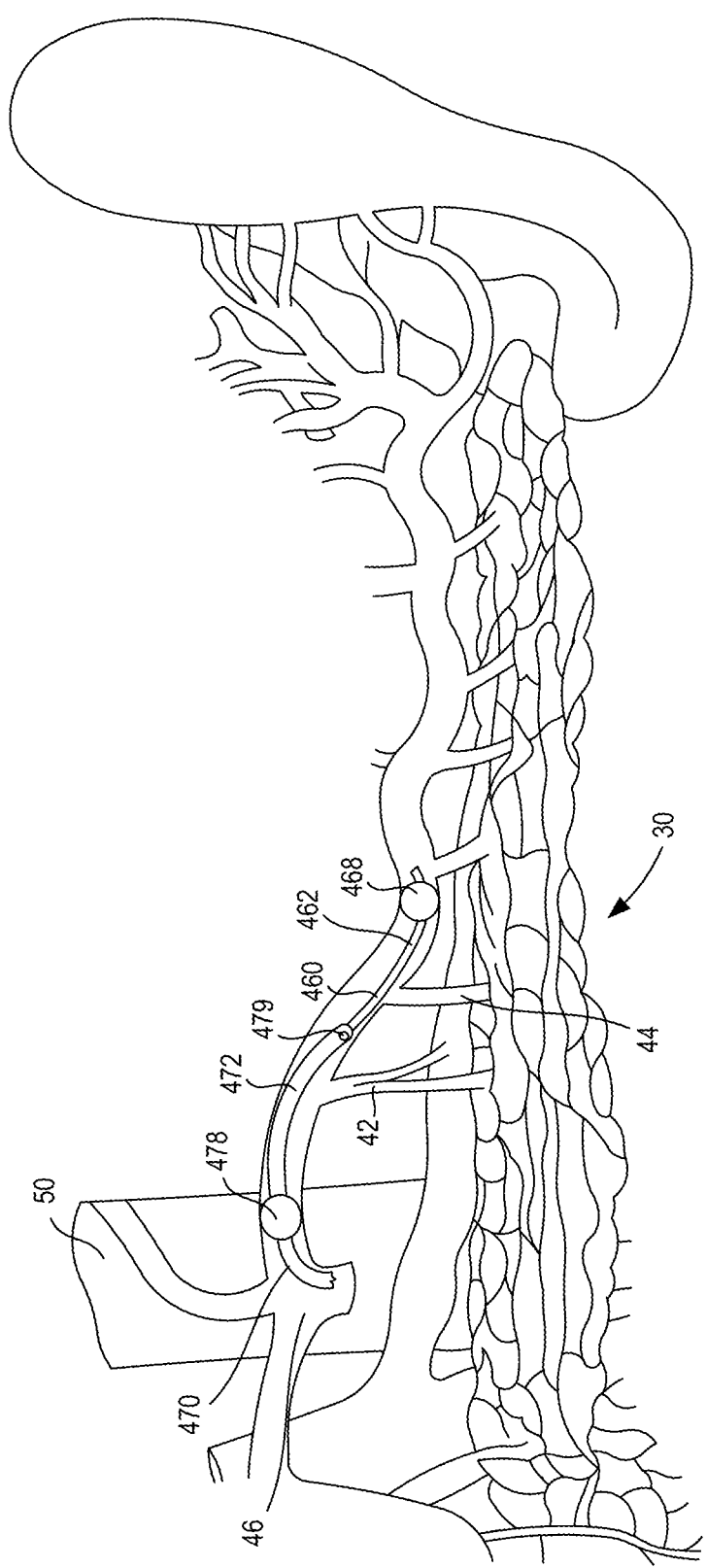
FIG. 30 is an illustration of a portion of the multi-occlusion catheter insertion device of FIG. 20 in use within a portion of a body.

In use, a guidewire can be inserted into the lumen 426 of the second port 425 and through the second lumen 465 defined by the first catheter 460. In this manner, the guidewire can be advanced through a bodily lumen and the device 400 can be manipulated to advance the first catheter 460 and the second catheter 470 along the guidewire. Thus, the distal end portion 462 of the first catheter 460 and the distal end portion 472 of the second catheter 470 can be placed at a target location within the bodily lumen such as, for example, the haptic or splenic artery of the pancreas, as shown in FIG. 30. At the target location, the actuator 450 can be moved between its first position and its second position relative to the handle 410 (e.g., the BB direction in FIG. 29) to define a desired distance (e.g., the distance D8 in FIG. 29) between the occlusion member 468 of the first catheter 460 and the occlusion member 478 of the second catheter 470. With the desired distance defined between the occlusion members 468 and 478, and with an inflation source coupled to the first port 420 and the same or a different inflation source coupled to the third port 430 (and/or the fourth port 435), the occlusion member 468 of the first catheter 460 and the occlusion member 478 of the second catheter 470, respectively, can be transitioned from a collapsed or deflated configuration to an expanded or inflated configuration to substantially isolate a segment of the bodily lumen disposed therebetween (e.g., the pancreatic segment or portion of the splenic artery 40 associated with, for example, the dorsal pancreatic artery 42 and/or the pancreatic magnum artery 44), as shown in FIG. 30. FIG. 30 is an illustration of the catheter device 400 disposed in situ within the splenic branch of the celiac artery. As shown in FIG. 30, the occlusion elements 468 and 478 define or isolate an area of interest in between the occlusion elements 468 and 478. Specifically, in this example, the region or area of interest with blood supply to the pancreas is isolated via the occlusion elements 468 and 478, spaced according to the location of the dorsal pancreatic artery 42 and the pancreatic magnum artery 44.

With the occlusion members 468 and 478 substantially occluding the body lumen, a biological/therapeutic agent can be delivered to the substantially isolated segment via the fifth port 440, the third lumen 476, and the opening 479 (i.e., the infusion aperture), into the area substantially isolated between the occlusion elements 468 and 478. In some instances, the substantially isolated segment can be irrigated by coupling an irrigation source to the fifth port 440. Thus, the irrigation can be delivered to the substantially isolated segment via the lumen 441 of the fifth port 440 and the third lumen 476, the channel 477, and the opening 479 of the second catheter 470. In some instances, such irrigation can be delivered prior to the delivery of the biological/therapeutic agent, after the delivery of the biological/therapeutic agent, or substantially concurrently with the biological/therapeutic agent.

Figure 31:
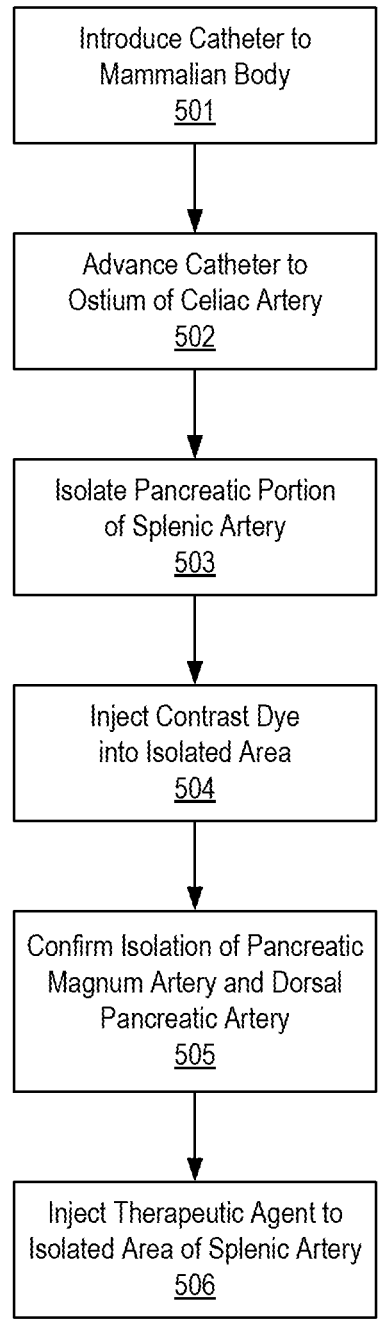
FIG. 31 is a flowchart illustrating a method for treating the pancreas, according to an embodiment.

FIG. 31 is a flowchart illustrating a method of accessing and treating a pancreas. The method can be used, for example, to occlude a portion of the splenic branch of the celiac artery supplying the pancreatic tail. The method includes introducing a catheter (e.g., the catheter device 100, 200, 300, and/or 400) into a mammalian body over a guidewire (211, 311) into a celiac artery, at 501. The catheter device can include an inner catheter (e.g., the first catheter 160, 260, 360, and/or 460) slidably coupled to an outer catheter (e.g., the second catheter 170, 270, 370, and/or 470). In some embodiments, a guide catheter can be exchanged over the guidewire into the celiac artery for support and introduction of the catheter device. After the guidewire is in place, the catheter device can be positioned over the guidewire, at 502, and positioned to allow placement of a distal occlusion element (e.g., the distal occlusion element 168, 268, 368, and/or 468) of the inner catheter at a distal edge of the pancreatic portion of the splenic artery (see, e.g., FIG. 30). The distal occlusion element and a proximal occlusion element (e.g., the proximal occlusion element 178, 278, 378, and/or 478) of the outer catheter are positioned to isolate a target portion of the pancreatic artery and moved to an expanded configuration, at 503. After the occlusion elements are deployed, contrast dye is injected through an injection port of the outer catheter and the isolated area of the splenic artery is visualized to identify the pancreatic branches, at 504. Visualization enables the clinician to confirm isolation of the pancreatic magnum artery and dorsal pancreatic artery or any other large artery supplying the pancreatic body or tail in the area, at 505. If desired, the catheter device can be moved back and the procedure repeated until the clinician can confirm that the catheter is correctly positioned. Some example isolation regions include: (a) the pancreatic magnum artery 44 (and its branches), (b) the dorsal pancreatic artery 42 if the origin is within the splenic artery 40, and (c) both pancreatic magnum artery 44 and dorsal pancreatic artery 42 arteries are isolated in one contiguous area (if other extra-pancreatic arteries do not arise between the origin of the two within the splenic artery 40).

After the first takeoff of the pancreatic magnum artery 44 is identified (or the dorsal pancreatic artery), the placement of the outer catheter of the catheter device can allow the edge of the distal occlusion element to be placed beyond this artery. At this point, the inner catheter can be secured in place, and the outer catheter can be moved relative to the inner catheter to allow the maximum perfusion area to the body and tail of the pancreas. Frequent injection of contrast through the infusion port can be made to ensure no extra-pancreatic vessels are included in the isolated area.

After the desired area is isolated and the occlusion elements are positioned at a desired location, the therapeutic cells/biologics/agent is introduced to the isolated area of the splenic artery through the infusion port of the outer catheter, at 506. The infusion port design can allow rapid and atraumatic infusion of cells/biologics/agent into the isolated area. This allows the clinician to adjust rate of infusion of therapeutic cells/biologics/agents into the isolated area based on specific pharmacodynamics and or engraftment efficiency requirements. The infusion of the therapeutic material can be followed by heparinized blood to exclude any residual cells left behind in the dead space of the catheter device. During isolation of the artery described above, perfusion to the end organ to the artery spleen can be disrupted, but the redundancy in the arterial perfusion system to the spleen, and limited time during which the arterial supply is interrupted, should prevent any long-term sequela, or abnormal condition of the splenic cells. If needed and/or desired, the guidewire port can be used to perform perfusion of the splenic artery beyond the isolated area. For example, the guidewire can be removed from its port after the catheter device is in place, and the guidewire port can be connected to a source of arterial blood with suitable pressure (i.e. the side port of an arterial sheath or guide sheath). At the end of the infusion, both occlusion elements are moved to a collapsed configuration and the catheter device is removed from the body over the guidewire as one unit, followed by the guidewire and the guide catheter.

In a variation of the method described above using balloons as the occlusion elements, the same catheter can be used to isolate arterial branches supplying the head of the pancreas via the hepatic artery or superior mesenteric artery. One such clinical possibility is treatment of pancreatic cancer with the tumor located in the head of the pancreas. After placement of the catheter device in the respective artery, the infusion of contrast through the infusion port can identify the branches most proximate to the tumor, and then after occluding the distal and proximal portion of the artery around the branch(es), the chemotherapeutic agent can be delivered selectively to the area of interest in the pancreas.

In some embodiments, a method can include introducing a catheter device into a splenic artery. The catheter device can include an inner catheter, a first expandable occlusion element coupled to the inner catheter, an outer catheter defining a first lumen configured to introduce a therapeutic biologic/agent to one or more target pancreatic vessels, a second lumen configured to slidably receive at least a portion of the inner catheter, and a second expandable occlusion element coupled to the outer catheter and disposed proximally to the first occlusion element. The catheter is advanced to a target pancreatic portion of the splenic artery. A region of the target pancreatic portion of the splenic artery is selectively isolated and the therapeutic biologic/agent is injected into the isolated region. In some embodiments, the therapeutic biologic/agent includes stem cells. In some embodiments, the method further includes advancing at least a portion of the catheter device to an ostium of a celiac artery, its hepatic branch, or if necessary, the superior mesenteric artery (based on individual anatomy). In some embodiments, a contrast dye is injected into the isolated region and isolation of a pancreatic magnum artery and/or a dorsal pancreatic artery can be confirmed. In some embodiments, a guidewire can be disposed through the infusion lumen to focally perforate the vascular lumen in the isolated area to increase exogenous cell penetration into the pancreatic tissue. In some embodiments, the therapeutic biologic can be introduced into the isolated segment or region to enhance cellular transmigration across the endothelial cells prior to introduction of the therapeutic biologic.

In some embodiments, a method can include introducing a catheter device into a bile duct. In use, the catheter device 200 can be placed at a desired location within the bile duct and used to infuse a therapeutic agents into the bile duct which will diffuse through the bile duct into the pancreas. A length of the first catheter 260 and the second catheter 270 can be adjusted such that a selected portion of the bile duct is isolated between the first occlusion element 268 and the second occlusion element 278. A therapeutic agent can be injected through the catheter device 200 and into the isolated region of the bile duct.

The infusion pressure in the isolated blood vessel region can be measured with pressure monitoring through the infusion lumen of the catheter (with a monometer (not shown) in line with infusion port 279). The pressure in the third lumen 276 can be based on the size of the agents being delivered, on the flow rate, the viscosity of the solution, and/or flow resistance of the third lumen 276 of second catheter 270. The flow resistance of the catheter device 200 can in turn be determined based on, for example, the inner coating material, the size and the length of the third lumen 276, the size of the third port 240, and/or the size of the distal infusion aperture 279. The catheter device 200 can allow for rapid infusion of agents (e.g., up to 2 milliliter per second (ml/sec)). In some applications, the rapid infusion can enhance uptake and eventual engraftment.

Any catheter device described herein and/or any combination of the catheter devices described herein can allow the above goals to be achieved. For example, a catheter device can include two catheters slidably coupled where an inner catheter defines a guidewire housing port and a distal occlusion element, and an outer catheter forms an infusion port and a proximal occlusion element, along with an inner lumen allowing the insertion of the inner catheter. The two catheters can be assembled outside the body with a distance between the two occlusion elements set to a desired length. For example, in some embodiments, the minimum distance between the two occlusion elements can be 3 cm, and the length can be adjusted up to a distance between the two occlusion elements of 25 cm as needed.

The devices described herein can also be provided in a kit. In some embodiments, a kit for use in the delivery of a biological agent to an area proximal to the pancreas can include, for example, one or more catheter devices (e.g., the catheter devices 100, 200, 300, and/or 400) as described herein and one or more biologic/therapeutic agent for delivery to the pancreas. The catheter devices can include, for example, a proximal end portion, a distal end portion and one or more expandable devices, such as a balloon or a filter, associated therewith. In some embodiments, the catheter device can include a first catheter configured to be slidably received within a lumen of a second catheter, a first occlusion element coupled to the first catheter and a second occlusion element coupled to the second catheter. In such an embodiment, a distance between the first and second occlusion elements can be varied or adjusted. The occlusion elements can be expandable to engage a wall of a blood vessel thereby substantially isolating an interior region of the vessel between the first and second occlusion elements. Moreover, the first and second catheters can be configured such that at least one of the first and second catheters has a lumen configured to deliver a biological/therapeutic agent to the isolated interior region via an infusion port. The infusion port can allow for rapid and atraumatic delivery of cells/biologics into the isolated area. In some embodiments, a pressure regulator can be provided that is configured to regulate the fluid pressure of the agent or the materials used to dilate the occlusion element(s) (e.g., in a balloon embodiment).

In some embodiments, a kit can further include one or more biologic/therapeutic agents for delivery to the pancreas, a stylet(s); one or more catheters adapted and configured for accessing the pancreatic vessels; a dilator; a guidewire; a guide catheter; capsules for direct connection of biological materials/cells to the infusion port of the delivery catheter; a manometer to monitor the pressure in the isolated area; and/or a pump to regulate the infusion rate of cells/biologics.

In some embodiments, any of the components of a kit can be packaged together and collectively sold as a catheter device or can be packaged independently or in subgroups and sold together or separately. For example, in some embodiments, the handle 410 can be packaged independently from the first catheter 460 and the second catheter 470. Moreover, the first catheter 460 and the second catheter 470 can be packaged independent from one another or packaged together. As such, the handle 410 can be sold independent of the first catheter 460 and the second catheter 470. The first catheter 460 and the second catheter 470 can be sold independent of one another or together. Thus, in some embodiments, the handle 410 can be packaged independent of the first catheter 460 and the second catheter 470 and, prior to use, can be coupled to the first catheter 460 and the second catheter 470 such that the first set of ports 428 are in fluid communication with the corresponding lumen of the first catheter 460 and the second set of ports 443 are in fluid communication with the corresponding lumen of the second catheter 470. In some embodiments, the handle 410 can be, for example, reusable, while the first catheter 460 and the second catheter 470 are disposable. In other embodiments, the handle 410 can be coupled to the first catheter 460 and the second catheter 470 during, for example, a manufacturing process and packaged together to be sold as a complete catheter device.

In some embodiments, placement of the occlusion elements (e.g., the distal occlusion elements 168, 268, 368, and/or 468 and the proximal occlusion elements 178, 278, 378, and/or 478) and the lengths of each region therebetween can be varied based on the needs of the individual application. The catheter devices 100, 200, 300 and/or 400 can retain sufficient trackability to allow advancement into the target region of the patient. In some embodiments, the catheter material can be flexible enough to traverse local anatomy yet have enough tensile strength to be able to be placed in position in place over a guidewire (e.g., the guidewire 280 and/or 380). Furthermore, for the first catheters 160, 260, 360, and 460 and the second catheters 170, 270, 370, and 470, respectively, to be slidable relative to each other in situ, various radial and tensile strengths can be incorporated in each.

The first catheters 160, 260, 360, and/or 460 (i.e., the inner catheters) and the second catheters 170, 270, 370, and/or 470 (i.e., the outer catheters) can be fabricated of any material suitable for catheters, such as linear low density or high density polyethylene, nylon, polyurethane, polypropylene, silicone rubber, or other non-thrombogenic materials. In some embodiments, an outer catheter can be formed from a linear low-density polyethylene, while an inner catheter can be formed from a nylon. In some embodiments, the outer catheters described herein can be fabricated to include a structure for reinforcement (not shown), such as a metal braid or the like located between an inner and outer layer. The reinforcement structure can extend along any desired length of such outer catheters. In some embodiments, a reinforcement structure can extend along the entire length of an outer catheter.

In some embodiments, regions of a first catheter (i.e., an inner catheter) such as those described herein can also be fabricated in any manner that allows the relative stiffness of each region to vary. In some embodiments, an outer layer in each region of an outer catheter and/or an inner catheter can include a material with a different durometer measurement of hardness. For example, the material used in an intermediate region can be relatively harder than that used in a distal region, and the material used in a proximal region can be relatively harder than that used in the intermediate region. Other manners of varying the stiffness of an inner catheter and/or an outer catheter (i.e., a first catheter and a second catheter, respectively, such as those described herein) can include varying the length of a reinforcement structure, varying the degree of reinforcement provided by the reinforcement structure along the length of the inner catheter and/or the outer catheter, changing a cross-sectional size and/or shape of the inner catheter and/or the outer catheter, introducing and/or forming one or more discontinuities along a length of the inner catheter and/or the outer catheter (e.g., one or more ribs, notches, grooves, protrusions, etc.), and/or any other suitable means for varying stiffness.

In some embodiments, the catheter devices described herein can include one or more sensors that can provide relative information such as, for example, position of the occlusion members, movement of the actuator, flow rate of the biological agent, and/or any other suitable information. For example, in some embodiments, a sensor can be operably coupled to the actuator 450 of the device 400 and can be configured to provide information associated with a distance that the actuator 450 has been moved. In such embodiments, a user and/or an electronic device can determine a distance between the occlusion member 468 of the first catheter 460 and the occlusion member 478 of the second catheter 470 based on the information from the sensor. In some embodiments, a sensor can be disposed within the third lumen 476 of the second catheter 470 that can be configured to determine a flow rate of irrigation and/or a biological/therapeutic agent therethrough.

In some embodiments, radiopaque markers of gold or tantalum, for example, can also be provided on or in an inner catheter positioned, within or on an occlusion element(s) (e.g., the occlusion elements 168, 178, 268, 278, 368, 378, 468, and/or 478), and/or on an outer catheter to aid in visualization and to assist in monitoring the position of at least a portion of a catheter device (e.g., the catheter devices 100, 200, 300, and/or 400) on an imaging device (e.g., a fluoroscope, an X-Ray, a Magnetic Resonance Imaging (MM) scan, a computerized tomography (CT) scan, and/or the like) during a procedure. In some embodiments, an inner catheter can optionally be coated with a lubricous material, such as silicone, acrylamide, or a hydrophilic polyurethane coating, to ease retraction. Similarly, the outer catheter and the occlusion elements can be coated with the lubricous material to ease advancement through a guiding catheter and/or a tortuous vessel.

In some embodiments, an outer diameter of an outer catheter (e.g., the second catheters 100, 200, 300 and/or 400) and non-deployed occlusion elements (e.g., the occlusion elements 168 and 178, 268 and 278, 368 and 378, and/or 468 and 478) can be, for example, between about 6 French and about 8 French and thus, can be used with, for example, a 7-9 French guiding catheter (if need be).

In some embodiments, after a guidewire (e.g., the guidewire 280 and/or 380) is removed, a corresponding lumen (e.g., the second lumen 165, 265, 365, and/or 465 of the first catheter 160, 260, 360, and/or 460, respectively) can be used to establish arterial blood flow distal to the occlusion end (e.g., the distal end portion) of a catheter device or infusion of other therapeutic agents if desired.

In some embodiments, any suitable configuration of the catheter devices can be used to achieve the objectives described herein including, for example, employing one or more catheter devices 100, 200, 300, and/or 400, employing a contiguous inflation/occluding section having differing stiffness along its length to achieve the two occluding elements, and/or the like.

In some embodiments, to allow endovascular isolation of the pancreatic portion of the splenic artery 40 (see e.g., FIG. 1) as a mechanism to achieve substantially exclusive delivery of a therapeutic agent/cells to the pancreatic parenchyma, a catheter device such as those described herein can include anatomical and mechanical features such as, for example, isolation of the two ends of the pancreatic portion of the artery using two occlusion elements; adjustment of the diameter of the occlusion elements to meet the specific anatomical needs; adjustment of the distance between the two occlusion elements (based on individual variation to selectively isolate for instance the portion of the splenic artery 40 to the pancreas 30 on one hand and maximize the perfusion area on the other hand); an infusion port where injection of contrast can be used to visualize the area of the artery isolated; an infusion port, shaft, and/or aperture design to allow atraumatic and rapid delivery of cells/therapeutic agents; and/or recovery of the occlusion element along with the catheter at the end of the procedure, prior to which flushes through the infusion port can assure clearance of the cells from the isolated space.

In some instances, any portion of the catheter devices 100, 200, 300, and/or 400 can be rotated to allow for a more targeted delivery of the biological/therapeutic agent to a selected tissue. For example, while the infusion apertures 279, 379 and 479 are shown as being disposed at a specific position relative to the pancreas 30, in some instances, the catheter device 100, 200, 300, and/or 400 can be rotated to rotate the second catheter 470 relative to the pancreas 30. Thus, the infusion aperture 279, 379, and/or 479 is rotated about a longitudinal axis (not shown) defined by the second catheter 270, 370, and/or 470. As such, the infusion aperture 279, 379, and/or 479 can be positioned adjacent to a target tissue for a more accurate delivery of the biological agent than would otherwise be possible. In some embodiments, any portion of the catheter device 200, 300, and/or 400 can include indicia and/or markings that can be associated with the relative position of the infusion aperture 279, 379, and/or 479. In this manner, a user can visualize the radial position of, for example, an actuator (e.g., the actuator 450) to determine the radial position of the infusion aperture 279, 379, and/or 479.

Any catheter device described herein and/or any combination of the catheter devices described herein can allow the above goals to be achieved. For example, a catheter device can include two catheters slidably coupled where an inner catheter defines a guidewire housing port and a distal occlusion element, and an outer catheter forms an infusion port and a proximal occlusion element, along with an inner lumen allowing the insertion of the inner catheter. The two catheters can be assembled outside the body with a distance between the two occlusion elements set to a desired length. For example, in some embodiments, the minimum distance between the two occlusion elements can be 3 cm, and the length can be adjusted up to a distance between the two occlusion elements of 25 cm as needed.

In some embodiments, a catheter device such as those described herein, which is suitable for accessing the pancreas 30 (see e.g., FIG. 1) can include features and/or functions, such as, for example, selective isolation of the targeted portion of the pancreatic portion of the splenic artery 40 for targeted delivery of the therapeutic agent to the pancreas 30; an adjustable distance between the two ends of the perfusion/infusion area (e.g., an isolated region) to accommodate individual anatomy to allow isolation of the largest portion of the splenic artery 40 with branches only supplying the pancreatic tail 32 and body 34 (see e.g., FIG. 1) and if clinically indicated, the same catheter can be used to isolate portions of the hepatic artery 54 and/or superior mesenteric artery 52 supplying the head of the pancreas 38; an infusion port allowing first, injection of contrast into the isolated segment to allow direct visualization of the origin of the branches of the splenic artery 40 supplying the pancreatic tissue, and second, introduction of therapeutic drugs/cells, the dimensions and design of the infusion port and catheter shaft allowing rapid and atraumatic delivery of cells; adjustable diameter of the proximal and/or distal occluders to allow both intravariable and intervariable sizes of the splenic artery 40; and/or a self-contained assembly unit with easy retrieval after completion of the procedure.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. For example, the size and specific shape of the various components can be different from the embodiments shown, while still providing the functions as described herein. Furthermore, each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

For example, although the outer catheters 170, 270, 370, and/or 470 of the catheter devices 100, 200, 300, and/or 400 include an infusion lumen (i.e., a third lumen) and infusion port and/or aperture to deliver a cell/biologic/therapeutic material to a desired blood vessel, in other embodiments, the inner catheter 160, 260, 360, and/or 460, respectively, can include the infusion lumen. Similarly, although the guidewire lumen (i.e., a second lumen) is described as being defined by the inner catheter 160, 260, 360, and/or 460, a guidewire lumen can be alternatively, or in addition to, included in and/or defined by the outer catheter 170, 270, 370, and/or 470. Thus, any of the lumens of the catheter devices 100, 200, 300, and/or 400 can be defined by either the first catheter 160, 260, 360, and/or 460 (i.e., an inner catheter) or the second catheter 170, 270, 370, and/or 470 (i.e., an outer catheter). In another example, although shown coupled to the second catheter 270 and/or 370, the sealing element 285 and/or 385 can alternatively be coupled to the first catheter 260 and/or 360.

Although the catheter devices 100, 200, 300, and/or 400 have been shown and described as having either two balloon occlusion elements or two filter elements, in alternative embodiments, a catheter device can include a combination of occlusion elements. For example, a catheter device such as those described herein can include one or more balloon occlusion elements (e.g., the balloon elements 268 and/or 278) and one or more filter element occlusion elements (e.g., the filter elements 368 and/or 378).

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. For example, the size and specific shape of the various components can be different from the embodiments shown, while still providing the functions as described herein. Furthermore, each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed is:

1. A kit, comprising:
   a chemotherapeutic agent; and
   a catheter device including:
   an inner catheter defining an inner catheter lumen configured to receive a guidewire;
   a first occlusion element coupled to the inner catheter at a first axial location along the catheter device;
   an outer catheter including a side wall defining an infusion aperture, the outer catheter defining a first lumen in fluid communication with the infusion aperture and a second lumen, a portion of the inner catheter being slidably disposed within the second lumen;
a second occlusion element coupled to the outer catheter at a second axial location along the catheter device, the second axial location spaced apart from the first axial location such that the infusion aperture is between the first occlusion element and the second occlusion element, the first occlusion element and the second occlusion element being configured to isolate a segment of a vessel; and
an adapter coupled to the outer catheter, the adapter including a first port and a second port, the first port in fluid communication with the first lumen through which the chemotherapeutic agent can be conveyed to the segment of the vessel isolated by the first occlusion element and the second occlusion element, the second port in fluid communication with the second lumen.

2. The kit of claim 1, wherein:
the vessel is a splenic artery; and
the second axial location is spaced apart from the first axial location by a distance associated with the splenic artery.

3. The kit of claim 2, wherein the distance is between 3 cm and 15 cm.

4. The kit of claim 1, wherein the catheter device further includes a pressure sensor disposed between the first occlusion element and the second occlusion element, the pressure sensor configured to measure a fluid pressure within the segment of the vessel isolated by the first occlusion element and the second occlusion element.

5. The kit of claim 1, wherein the catheter device includes a sealing element coupled to the outer catheter between the inner catheter and the outer catheter, the sealing element configured to prevent the chemotherapeutic agent from entering the second lumen of the outer catheter.

6. The kit of claim 1, wherein:
the first occlusion element and the second occlusion element are each configured to be transitioned from a collapsed configuration to an expanded configuration, the first occlusion element and the second occlusion element isolating the segment of the vessel when each of the first occlusion element and the second occlusion element are in their expanded configuration; and
the adapter includes a third port fluidically coupled to the second occlusion element, the second port configured to convey an inflation medium to the second occlusion element to transition the second occlusion element from its collapsed configuration to its expanded configuration.

7. The kit of claim 1, wherein the catheter device includes a pressure monitoring port in line with the infusion aperture and through which an infusion pressure within the isolated segment of the vessel between the first occlusion element and the second occlusion element can be measured.

8. A kit, comprising:
a chemotherapeutic agent; and
a catheter device including:
an inner catheter including a first occlusion element, the inner catheter defining an inner catheter lumen and an opening at a distal end of the inner catheter in fluid communication with the inner catheter lumen and an environment exterior to the inner catheter and the first occlusion element;
an outer catheter including a second occlusion element and a side wall, the side wall defining an infusion aperture, the outer catheter defining a first lumen in fluid communication with the infusion aperture and a second lumen within which a first portion of the inner catheter is slidably received, the second occlusion element spaced apart from the first occlusion element by a distance such that the first occlusion element and the second occlusion element are configured to isolate a segment of a vessel; and
an adapter coupled to the outer catheter, the adapter including a first port and a second port, the first port in fluid communication with the first lumen through which the chemotherapeutic agent can be conveyed to the segment of the vessel isolated by the first occlusion element and the second occlusion element, the second port configured to receive a second portion of the inner catheter,
the catheter device configured to be coupled to a pressure sensor to monitor an infusion pressure within the segment of the vessel isolated by the first occlusion element and the second occlusion element.

9. The kit of claim 8, wherein the first port is configured to be coupled to a pressurized delivery source containing the chemotherapeutic agent.

10. The kit of claim 9, further comprising:
a pressure regulator configured to regulate the infusion pressure when the chemotherapeutic agent is conveyed to the segment of the vessel isolated by the first occlusion element and the second occlusion element.

11. The kit of claim 9, further comprising:
the pressure sensor, the pressure sensor being disposed between the first occlusion element and the second occlusion element.

12. The kit of claim 8, wherein the catheter device is configured to be manipulated to adjust the distance.

13. The kit of claim 12, wherein the inner catheter is configured to move within the second lumen to adjust the distance.

14. The kit of claim 8, wherein the catheter device includes a sealing element coupled between the inner catheter and the outer catheter and configured to prevent the chemotherapeutic agent from entering the second lumen of the outer catheter.

* * * * *

UNITED STATES PATENT AND TRADEMARK OFFICE
CERTIFICATE OF CORRECTION

PATENT NO. : 10,512,761 B2
APPLICATION NO. : 15/351922
DATED : December 24, 2019
INVENTOR(S) : Ramtin Agah et al.

Page 1 of 1

It is certified that error appears in the above-identified patent and that said Letters Patent is hereby corrected as shown below:

On the Title Page

Item (54); delete "METHODS FOR DELIVERY OF THERAPEUTIC MATERIALS TO TREAT PANCREATIC CANCER" and insert --METHODS FOR DELIVERY OF THERAPEUTIC MATERIALS TO TREAT CANCER--.

In the Specification

Column 1, Lines 1-3; delete "METHODS FOR DELIVERY OF THERAPEUTIC MATERIALS TO TREAT PANCREATIC CANCER" and insert --METHODS FOR DELIVERY OF THERAPEUTIC MATERIALS TO TREAT CANCER--.

Signed and Sealed this
Twenty-fifth Day of February, 2020

Andrei Iancu
*Director of the United States Patent and Trademark Office*